(12) United States Patent
Curiel

(10) Patent No.: US 6,955,808 B2
(45) Date of Patent: Oct. 18, 2005

(54) CAPSID-MODIFIED RECOMBINANT ADENOVIRUS AND METHODS OF USE

(75) Inventor: David T. Curiel, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/668,453

(22) Filed: Sep. 23, 2003

(65) Prior Publication Data

US 2004/0081637 A1 Apr. 29, 2004

Related U.S. Application Data

(60) Continuation-in-part of application No. 10/424,409, filed on Apr. 28, 2003, which is a division of application No. 09/668,791, filed on Sep. 22, 2000, now Pat. No. 6,555,368.
(60) Provisional application No. 60/156,104, filed on Sep. 24, 1999.

(51) Int. Cl.$^7$ .................. A61K 48/00; C12N 15/00; C12N 15/86; C07N 21/04
(52) U.S. Cl. ................ 424/93.2; 435/320.1; 435/456; 536/23.1; 536/23.4
(58) Field of Search ............... 424/93.2; 435/320.1, 435/456; 536/23.1, 23.4

(56) References Cited

U.S. PATENT DOCUMENTS

| | | | |
|---|---|---|---|
| 5,723,287 A | 3/1998 | Russell et al. | |
| 5,846,782 A | 12/1998 | Wickham et al. | |
| 5,871,727 A | 2/1999 | Curiel | |
| 6,740,525 B2 | 5/2004 | Roelvink et al. | |

FOREIGN PATENT DOCUMENTS

| | | | |
|---|---|---|---|
| GB | 99/36545 | | 7/1999 |
| WO | WO 97/20051 | * | 6/1997 |
| WO | WO 99/36545 | * | 7/1999 |

OTHER PUBLICATIONS

Boudin et al. Human adenovirus type 2 protein IIIa. Virology 101:144–156, 1980.*
Alemany et al. CAR–binding ablation does not change biodistribution and toxicity of adenoviral vectors. Gene therapy 8:1347–1353, 2001.*
Martin et al. Simultaneous CAR– and alphav Integrin–binding ablation fails to reduce Ad5 liver tropism. Mol. Therapy 8:485–494, 2003.*
Akalu et al. The subgenus–specific C–terminal region of protein IX is located on the surface of the adenoviral capsid. J. Virol. 73:6182–6187, 1999.*
Wickham et al. Increased in vitro and in vivo gene transfer by adenovirus vectors containing chimeric fiber proteins. J. Virol. 71:8221–8229, 1997.*
Weissleder & Ntziachristos, "Shedding light onto live molecular targets," Nature Medicine 9(1):123–128 (2003).
Curiel, D. et al., "Strategies to Adapt Adenoviral Vectors for Targeted Delivery," Ann. NY Acad. Sci., 886: 158–71, 1999.
Dang et al., "Gene Therapy and Translational Cancer Research," Clinical Cancer Research, 5: 471–74, 1999.
Deonarain, "Ligand–Targeted Receptor–Mediated Vectors for Gene Delivery," Exp. Opin. Ther. Patents, 8(1):53–69, 1998.
Douglas, J. et al., "A system for the propagation of adenoviral vectors with genetically modified receptor specificities," Nat. Biotechnl., 17:470–75.
Krasnykh, V. et al., "Generation of Recombinant Vectors with Modified Fibers for Altering Viral Tropism," J. Virol., 70:6839–46, 1996.
Manuel Rosa–Calatrava et al., "Functional Analysis of Adenovirus Protein IX Identifies Domains Involved in Capsid Stability, Transcriptional Activity, and Nuclear Reorganization," J. Virol., 75:7131–41, 2001.
Meng et al., "Tumor Suppressor Genes as Targets for Cancer Gene Therapy," Gene Therapy of Cancer, 3–20, 1999.
Miller et al., "Targeted Vectors for Gene Therapy," FASEB J., 9:190–99, 1995.
Ngo et al., "Computational Complexity, Protein Stucture Prediction, and the Levinthal Paradox," In: Protein Folding Problem and Teritary, Stucture Prediction (Merz et al., eds.), Birkhauser, Boston, pp. 419–494, 1994.
Peng et al., "Viral Vector Targeting," Current Opinion in Biotechnology, 10: 454–57, 1999.
Rudinger, "Characteristics of the Amino Acids as Components of a Peptide Hormone Sequence," In: Peptide Hormones (Parsons, J.A., ed.), University Park Press, Baltimore, pp. 1–7, 1996.
Verma, et al., "Gene Therapy—Promises, Problems and Prospects," Nature, 389: 239–42, 1997.
Wickham, T. et al., "Targeted Adenovirus Gene Transfer to Endothelial and Smooth Muscle Cells by Using Bispecific Antibodies," J. Virol., 70: 6831–38, 1996.

(Continued)

Primary Examiner—David Guzo
Assistant Examiner—Quang Nguyen
(74) Attorney, Agent, or Firm—Frommer Lawrence & Haug; Thomas J. Kowalski; Deborah L. Lu

(57) ABSTRACT

The present invention describes recombinant adenoviral vectors modified by incorporating targeting ligands or label into viral capsid or structural proteins. In one embodiment, single-chain antibody was introduced into the minor capsid proteins pIIIa or pIX so that the adenoviral vector can be targeted to a particular cell type. In another embodiment, there is provided a noninvasive imaging strategy useful for monitoring the replication and spread of conditionally replicative adenoviral vectors. Viral structural proteins such as pIX capsid protein, core proteins mu, V and VII were expressed as fusion protein with a fluorescent label. Once incorporated into the virions, detection of the structural fusion protein label would indicate the localization of the disseminated viral progeny. The detected fluorescent signals also closely correlate with the level of viral replication and progeny production.

13 Claims, 17 Drawing Sheets

OTHER PUBLICATIONS

Wickham, T. et al., "Targeted Adenovirus–Mediated Gene Delivery to T Cells via CD3," J. Virol., 71: 7663–69, 1997.

Balague C et al., Human papillomavirus E6E7–mediated adenovirus cell killing:selectivity of mutant adenovirus replication in organotypic cultures of human keratinocytes, J. Virol. 75:7602–11 (2001).

Bevis and Glick, Rapidly maturing variants of the Discosoma red fluorescent protein (DsRed), Nat Biotechnol. 20:83–7 (2002).

Bhaumik and Gambhir, Optical imaging of Renilla luciferase reporter gene expression in living mice, Proc Natl Acad Sci USA, 99:377–82 (2002).

Burclo et al., Detecting protein—protein interactions using Revilla luciferase fusion proteins. Biotechniques 33:1044–8, 1050 (2002).

Campbell et al., A monomeric red fluorescent protein, Proc Natl Acad Sci USA, 99:7877–82 (2002).

Chartier et al., Efficient generation of recombinant adenovirus vectors by homologous recombination in *Escherichia coli*, J. Virol. 70:4805–4810 (1996).

Chaudhuri et al., A noninvasive reporter system to image adenoviral–mediated gene transfer to ovarian cancer xenografts. Gynecol Oncol. 83:432–8 2001).

Chaudhuri et al., Light–based imaging of green fluorescent protein–positive ovarian cancer xenografts during therapy. Gynecol Oncol. 82:581–9 (2001).

Diehn et al., Noninvasive fluorescent imaging reliably estimates biomass in vivo. Biotechniques 33:1250–2, 1254–5 (2002).

Dmitriev et al., Engineering of adenovirus vectors containing heterologous peptide sequences in the C terminus of capsid protein IX. J Virol. 76:6893–9 (2002).

Gross et al., The structure of the chromophore within DsRed, a red fluorescent protein from coral, Proc Natl Acad Sci USA. 97:11990–5 (2000).

Gurskaya et al., GFP–like chromoprotein as a source of far–red fluorescent proteins. FEBS Lett. 507:16–20 (2001).

He et al., A simplified system for generating recombinant adenoviruses, Proc Natl Acad Sci USA, 95:2509–14 (1998).

Hoffman, Visualization of GFP–expressing tumors and metastasis in vivo. Biotechniques 30:1016–22, 1024–6 (2001).

Hyin et al., Fiber–optic monitoring coupled with confocal microscopy for imaging gene expression in vitro and in vivo. J Neurosci Methods 108:91–6 (2001).

Rooney et al., Laser fluorescence bronchoscopy for detection of fluorescent reporter genes in airway epithelia, Gene Ther. 9:1639–44 (2002).

Wang et al., Renilla luciferase–Aequorea GFP (Rue–GFP) fusion protein, a novel dual reporter for real–time imaging of gene expression in cell cultures and in live animals, Mol. Genet Genomics 268:160–8 (2002).

Weissleder and Mahmood, Molecular imaging, Radiology 219: 316–33 (2001).

Yamamoto et al., Infectivity Enhanced, Cyclooxgenase–2 Promoter–Based Conditionally Replicative Adenovirus for Pancreatic Cancer, Gastroenterology, 125(4):1203–18 (2003).

Yang et al., Whole–body optical imaging of green fluorescent protein–expressing tumors and metastases. Proc Natl Acad Sci USA. 97:1206–11 (2000).

Yang et al., Visualizing gene expression by whole–body fluorescence imaging, Proc Natl Acad Sci USA 97:12278–82 (2000).

Yang et al., Direct external imaging of nascent cancer, tumor progression, angiogenesis, and metastasis on internal organs in the fluorescent orthotopic model. Proc Natl Acad Sci USA. 99:3824–9 (2002).

* cited by examiner

30 min post-infection

1-2 hours post-infection

Ad-ΔE1-IX-EGFP-ΔE3 0.1 fcu/cell

Ad-wt-IX-EGFP 0.1 fcu/cell 0.01 fcu/cell 0.01 fcu/cell

CAPSID-MODIFIED RECOMBINANT ADENOVIRUS AND METHODS OF USE

CROSS-REFERENCE TO RELATED APPLICATION

This continuation-in-part application claims the benefit of priority of application Ser. No. 10/424,409, filed Apr. 28, 2003, which is a divisional application of Ser. No. 09/668,791 filed on Sep. 22, 2002, now U.S. Pat. No. 6,555,368, which claims the benefit of priority of application 60/156,104, filed Sep. 24, 1999, now abandoned.

BACKGROUND OF THE INVENTION

1. Field of the Invention

The present invention relates generally to modification of adenoviral gene therapy vectors and uses thereof. In one embodiment, the present invention discloses modified adenoviral vectors that have altered tropism. In another embodiment, there is provided fluorescently labeled adenoviral vectors useful for monitoring viral vector distribution.

2. Description of the Related Art

Adenoviral vectors (Ad) have proven to be of enormous utility for a variety of gene therapy applications. This usefulness is derived largely from the unparalleled delivery efficiency of these vectors for in vitro and in vivo applications. Despite this property, however, the full benefit of these vectors is undermined currently by the lack of cell-specific gene delivery capability. Specifically, the promiscuous tropism of the adenovirus hinders gene delivery in a targeted, cell-specific manner. Thus, for the many gene therapy applications where such cell-specific transduction is required, current adenoviral vectors have limited utility.

To address the issue of efficient, cell-specific gene delivery, a variety of strategies have been developed to alter adenoviral tropism. These approaches have included direct chemical modifications of the adenoviral capsid proteins, bi-specific complexes (i.e., a capsid protein and a targeting moiety), and genetic capsid modifications (i.e., genetic replacement/insertion). Whereas the former two strategies have established the feasibility of adenoviral re-targeting, practical production issues as well as regulatory approval considerations have placed the utmost importance on the approach in which modifications to the adenoviral tropism are introduced genetically.

To this end, methods that alter adenoviral tropism via modifications of the adenoviral major capsid proteins, fiber, penton and hexon have expanded tropism such that it is independent of the native adenoviral receptor (CAR). These methods additionally ablate the native tropism of the adenovirus. Experimentally, tropism expansion has been achieved via the incorporation of peptide ligands with specificity for target cellular markers. This has largely been via the incorporation of the peptide, RGD-4C, at fiber and hexon locales. RGD-4C recognizes integrins of the $\alpha v \beta 3$ and $\alpha v \beta 5$ classes. In addition, other small peptide markers have been employed to the same end. These studies have established that genetic modification(s) to the capsid can indeed alter adenoviral vector tropism to achieve a limited and/or specific range of gene delivery.

Of note, the locales employed in the context of modifying the major capsid proteins for targeting purposes have allowed only the incorporation of small peptides. To date, these have consisted of peptides identified via phage display methods, or short physiologic peptide ligands. Both of these types of targeting motifs, however, are suboptimal with respect to accomplishing the goal of cell-specific delivery. With respect to the former, only an extremely limited repertoire of useful peptides have been identified heretofore via phage display techniques. In addition, these peptides have tended to be of low affinity. Furthermore, the fidelity of such targeting peptides, when in the context of the adenoviral vector, is not always preserved. With respect to the latter, available physiologic peptides do not allow targeting to the range of cells required for practical gene therapy approaches.

In this regard, single chain antibodies (scFvs) represent motifs with highly diverse specificities that can be exploited for adenoviral targeting. In addition, single chain antibodies possess high affinities for cognate targets. On this basis, the ability to incorporate single chain antibodies into the adenoviral capsid, and for the single chain antibody specificity/affinity to be preserved following display of the chimeric/recombinant capsid protein would dramatically enhance the utility of genetic capsid modification methods for adenoviral retargeting. The inability to configure single chain antibodies at fiber, hexon, and penton locales has indicated the need to examine the ability of single chain antibodies to be incorporated into alternate capsid proteins.

Thus, the prior art is deficient in modification of adenoviral vectors that allows for genetic introduction of a useful targeting moiety. The present invention fulfills this long-standing need and desire in the art.

SUMMARY OF THE INVENTION

The present invention describes incorporation of single chain antibodies into the "minor" capsid proteins, pIIIa and pIX of adenovirus. pIIIa and pIX are present on the adenoviral capsid as monomers and the proteins have extended amino-terminus ectodomains. Thus, both locale and structural considerations indicate that pIIIa and pIX are the ideal capsid proteins for incorporating single chain antibodies and achieving genetic modification and retargeting of the adenovirus.

Accordingly, one object of the present invention is to provide a genetically modified adenovirus vector with cell-specific targeting capability and methods of making this genetically modified adenovirus vector.

The present invention also provides modified adenoviral vectors useful for noninvasive imaging to monitor the replication and spread of replicative adenoviral vectors. Adenoviral vectors are genetically modified to comprise a structural protein expressed as a fusion protein with a fluorescent label. Most of the adenoviral structural proteins are expressed late in the replication cycle. Therefore, the presence of late capsid and core structural proteins would indicate active replication beyond such early events as adsorption, penetration, transcription, and translation of early genes. Furthermore, the amount of detected structural proteins would correlate with the quantity of progeny production due to their direct involvement in the assembly of viral particles. Once incorporated into the virions, detection of the structural fusion protein label would indicate the localization of the disseminated viral progeny. Taken together, the use of a structural fusion protein label provides the advantages of detecting both viral replication and spread which is not possible in a strategy employing a reporter alone.

Adenoviruses can be labeled in one of two ways: capsid protein labeling and core protein labeling. Enhanced green fluorescent protein (EGFP) is chosen as the reporter because of its relatively small size (720 bp, 27 kDa), numerous applications as a versatile reporter in fusion constructs with various configurations, and potential for noninvasive imaging. Capsid labeling can be accomplished by fusing EGFP to the C-terminus of pIX, a locale that has already been utilized for incorporation of heterologous peptides. To label the adenoviral core, EGFP fusions with proteins mu, V, and VII can be employed.

In one embodiment, the fluorescent labels were incorporated into virions as pIX-EGFP fusion proteins that allowed detection of individual particles. Ad-IX-EGFP binding and infection could both be detected via the fluorescent label. Even though DNA packaging and progeny yield were marginally affected, the pIX-EGFP label did not affect DNA replication as well as overall viral cytopathic effect. Notably, the level of pIX-EGFP fluorescence directly correlated with the amount of progeny production due to its dependence on E1 activity for expression. The data with pIX-EGFP fulfills all the requirements of an ideal monitoring system for replicative adenoviruses. This labeling approach can easily be adapted to generate fluorescent viruses at high titers for assessing in vivo targeting functionality.

The capsid-labeling and core-labeling approaches disclosed herein offer great promise for detecting the replication and spread of replicative adenoviral vectors. Moreover, since this labeling method is biologically based, it can be applied to oncolytic adenoviral agents to achieve both temporal and spatial monitoring and provide information about viral replication and localization. The ability to acquire these data will assist in the evaluation and development of these viral agents for clinical usages.

Other and further aspects, features, and advantages of the present invention will be apparent from the following description of the presently preferred embodiments of the invention. These embodiments are given for the purpose of disclosure.

DETAILED DESCRIPTION OF THE INVENTION

Figure 1:
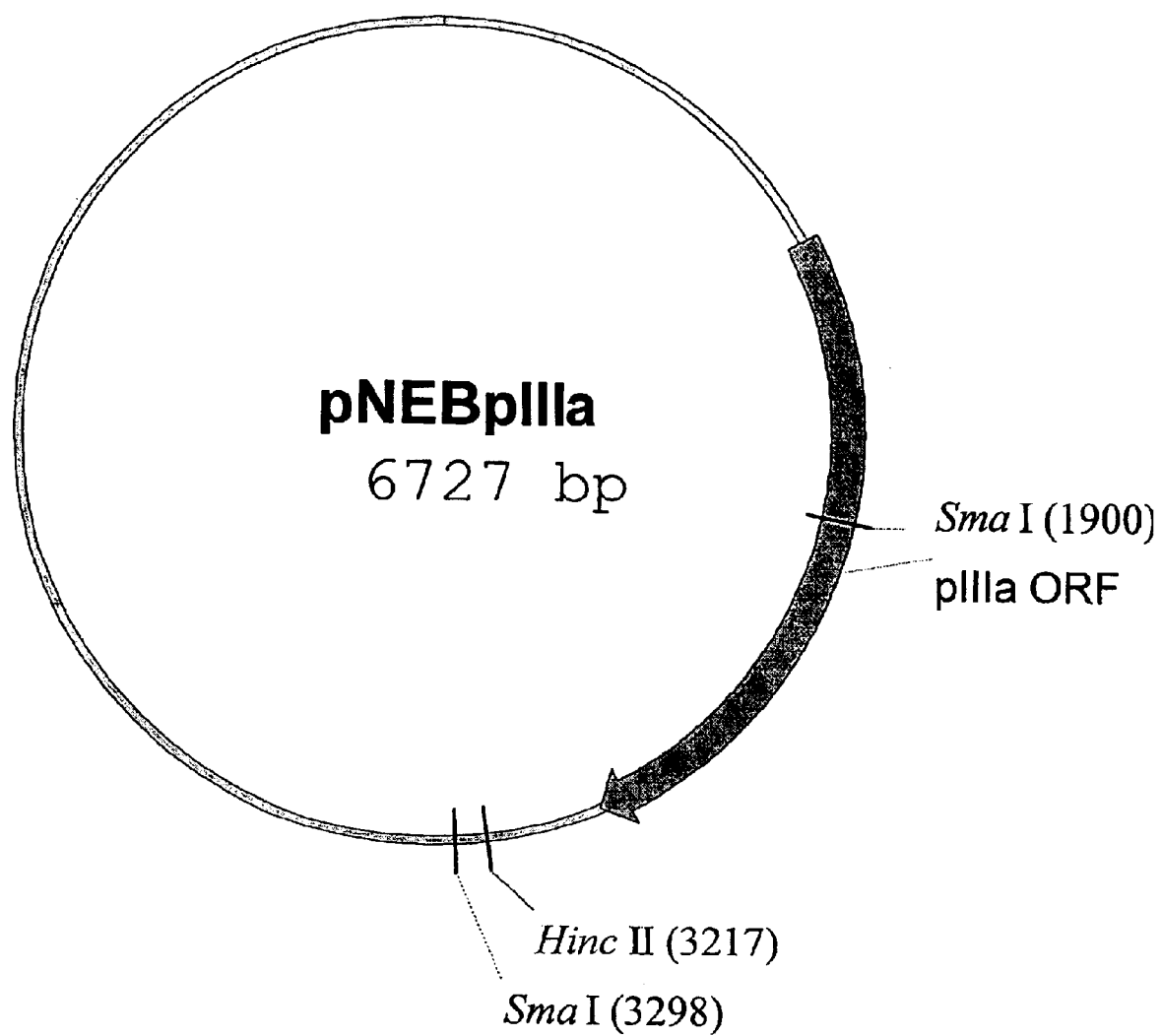
FIG. 1 shows the diagram of plasmid pNEBpIIIa.

The present invention describes incorporation of single chain antibodies and other targeting peptides into alternate adenoviral capsid proteins. In this regard, the adenovirus contains several "minor" capsid proteins in addition to the fiber, hexon and penton major capsid proteins. To be useful for adenoviral re-targeting purposes, candidate capsid proteins must possess domains that are associated with the surface of the adenoviral virion. Two such capsid proteins are pIX and pIIIa. Minor capsid proteins pIX and pIIIa exhibit unique structural characteristics consistent with the requirements of adenoviral retargeting via genetic capsid modification. In one embodiment, pIIIa and pIX capsid proteins are the ideal candidate capsid proteins for incorporation of scFvs to achieve genetic modification and re-targeting.

The present invention is directed towards a recombinant adenovirus comprising a modified gene encoding an adenoviral capsid protein. Preferably, the capsid gene is a minor capsid gene, and more preferably, the minor capsid genes are pIIIa and pIX. Generally, the modified capsid protein retains its native display profile. Typically, the recombinant adenovirus comprising the modified capsid gene exhibits CAR-independent gene transfer. Additionally, the present invention is directed towards a recombinant adenovirus comprising the modified capsid gene and further comprising an additional modification to an adenovirus fiber knob, wherein the modification to the fiber knob thereby ablates the native tropism of the adenovirus.

Typically, the gene encoding the capsid protein is modified by introducing a single chain antibody or other targeting peptide into the gene. Preferably, the single chain antibody is directed towards a protein specific to a cell type, and more preferably, the protein is a cell-surface protein. Generally, the cell type is a tumor cell. The present invention also provides for a recombinant adenovirus described herein containing a modified gene encoding a capsid protein and further comprising a therapeutic gene.

In instances when the recombinant adenovirus further comprises a therapeutic gene, the present invention is additionally directed towards a method of providing gene therapy to an individual in need of such treatment, comprising the steps of: administering to the individual an effective amount of a recombinant adenovirus, wherein the adenovirus comprises a modified gene encoding an adenoviral capsid protein. A representative example of therapeutic gene is herpes simplex virus-thymidine kinase. When the above-embodied therapeutic gene encodes a herpes simplex virus-thymidine kinase, the instant invention is further directed towards a method of killing tumor cells in an individual by administering to the individual an effective amount of the appropriate recombinant adenovirus and treating the individual with ganciclovir.

It is specifically contemplated that pharmaceutical compositions may be prepared using the novel genetically modified adenoviral vector of the present invention. In such a case, the pharmaceutical composition comprises the novel genetically modified adenoviral vector of the present invention and a pharmaceutically acceptable carrier. A person having ordinary skill in this art would readily be able to determine, without undue experimentation, the appropriate dosages and routes of administration of this genetically modified adenoviral vector of the present invention. When used in vivo for therapy, the genetically modified adenoviral vector of the present invention is administered to the patient or an animal in therapeutically effective amounts, i.e., amounts that eliminate or reduce the tumor burden.

The dose and dosage regimen will depend upon the nature of the cancer (primary or metastatic) and its population, the characteristics of the particular genetically modified adenoviral vector, e.g., its therapeutic index, the patient, the patient's history and other factors. The amount of genetically modified adenoviral vector administered will typically be in the range of about $10^9$ to about $10^{12}$ particles.

The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference.

The present invention also provides a genetic adenovirus capsid/core labeling system devised to offer unprecedented noninvasive dynamic imaging of conditionally replicative adenovirus replication and spread in vivo. Not only would this tool be indispensable in the preclinical development of advanced generation of conditionally replicative adenoviruses, but it would also be practical in the clinical setting to monitor the application of these agents for cancer therapy.

Current Vector Detection Methods are Inadequate for Replicative Systems

Conditionally replicative adenoviruses (CRAds) represent an important novel approach for cancer therapy. CRAd agents are designed to specifically replicate in and kill tumor cells to yield an effective yet safe therapeutic outcome. Little data have been obtained with regards to the critical functions of conditionally replicative adenoviruses, namely efficient infection of tumor cells, tumor-specific replication and lateral spread.

Limited understanding on the behavior of conditionally replicative adenoviruses in patients is attributed to lack of a noninvasive imaging system for monitoring the replicative agents. Several studies have attempted to address this problem, including a group who utilized positron emission tomography scanning to detect thymidine kinase as a reporter of oncolytic herpes simplex virus replication. Detection was restricted to infected cells expressing the reporter gene which does not truly represent the physical distribution of the virus itself. Another group employed soluble hCEA and hCG peptide markers as a way to monitor oncolytic measles virus therapy in mice which correlated with therapeutic outcome but cannot show viral localization.

Other conventional imaging systems for gene therapy have been designed for the detection of transgene expression using such reporters as GFP (green fluorescent protein), SSTR-2 (somatostatin receptor type 2), sodium iodide symporter, luciferase, and thymidine kinase. Despite their utility for assessing gene delivery and expression, these reporters by themselves are not suitable for monitoring the activity of replicative adenoviruses. The essence of oncolytic virus function is to infect and kill target cells, a concept that is at odds with reporter gene expression. Moreover, reporter gene expression may not truly represent the underlying level of viral replication and the physical distribution of viral progeny. No completed clinical trials so far have incorporated a monitoring component into replicative agents and therefore have had to rely on conventional histology of biopsy specimens and analysis of body fluids for the detection of virus. Such static assessments fall short of accurately depicting the dynamic mechanism of replicative agents.

Imaging and Monitoring of Conditionally Replicative Adenoviruses

The ideal system for monitoring conditionally replicative adenoviruses (CRAds) and other oncolytic viruses should meet a number of criteria. First, the detected signal should correlate with the level of viral replication or progeny production. Second, the signal should be directly associated or packaged with the virions to allow direct physical detection of viral dispersion. Third, the monitoring system needs to be self-perpetual in that produced virions as well as their progeny would be detected, allowing multi-time-point and multi-generational imaging of the "viral mass" that accrues from the initial dose. Fourth, the approach should minimally disrupt the replication and spread efficiency of the virus. Lastly, the detectability should be sufficient for noninvasive imaging of the replication events. Such a system would provide the flexibility for dynamic detection of both viral replication and spread to yield valuable and meaningful data.

Capsid Protein IX is a Potential Locale for Labeling Adenovirus

Genetic labeling of adenovirus through the fusion of a reporter with a structural protein warrants a number of considerations. First, the incorporation efficiency of a structural fusion protein into virions and hence its copy number per virion should be of sufficiency to give optimal detection of viral particles. An estimate of 20 copies of fluorophores per virion has been reported for adenoviral particle visualization. Second, fusion with the candidate protein should minimally perturb its cellular localization as well as its normal function. This requirement would maximize the possibility for incorporation and also preserve the function of the protein for viral replication. Third, the structural protein fusion label should provide a signal correlating with viral replication and progeny production.

Based on copy number and previous reports, the capsid protein IX is a potential locale for labeling adenovirus. Protein IX is a small polypeptide of 140 residues (14.7 kDa) that acts as a cement protein to stabilize hexon-hexon interaction and therefore the capsid structure itself. Four trimers of pIX interact with a group of nine hexons (GON) in each facet of the icosahedron, resulting in 240 copies of the protein per virion. In addition, pIX also serves as a transcriptional activator of several viral and cellular TATA-containing promoters, including adenoviral E1a, E4, and major late promoters. Based on the elucidation that the pIX C-terminus is surface exposed, pIX has been exploited as a locale to incorporate heterologous peptides (namely lysine octapeptide and polylysine) into its C-terminus for retargeting purposes. A single chain variable fragment (scFv) against the c-erbB-2 oncoprotein was also successfully fused to pIX and assembled into virions (I. Dmitriev, personal communication). Based on these initial data, it was hypothesized that pIX would be a suitable locale for incorporating a reporter protein like enhanced GFP (EGFP).

Core Proteins Mu, V, and VII are Potential Locales for Labeling Adenovirus

Due to interest in retargeting, numerous attempts have been made to genetically modify the adenoviral capsid. In contrast, the adenoviral core has not been exploited to such degree. Although of obvious non-utility for targeting, the core proteins may serve as promising targets for labeling adenovirus. The adenovirus core is composed of the viral genome and four core proteins. The terminal protein (TP) is covalently linked to the 5' end of each linear viral DNA strand at two copies per virion and as a 80 kDa premature form that gets processed into a 55 kDa mature version by the adenovirus protease during maturation. Its roles include matrix attachment, activation of transcription, distortion of origin structure, and stabilization of preinitiation complex.

Noncovalently and nonspecifically bound to the viral DNA through arginine-rich portions are three other core proteins mu, V, and VII. Protein VII is the major core protein contributing roughly 833 copies per virion. Expressed as a 174 amino acid precursor form from which a 23 amino acid N-terminus is cleaved, it serves as a histonelike center around which viral DNA is wrapped to form nucleosome structures. Interacting with protein VII is the minor core protein V which is thought to form a linkage between the DNA core and the capsid through association with protein VI. There are about 157 copies of protein V per virion which binds nonspecifically to the viral DNA. Protein V also associates with another minor core protein called mu. Cleaved from a 79-residue precursor, this highly basic protein of only 19 amino acids binds to DNA very tightly, suggesting that it plays a role in viral chromosome condensation. The copy number per virion of protein mu is not known.

The fusion of pV-EGFP has been shown to localize to the nucleus and nucleoli and that it redistributes nucleolin and B23 from the nucleolus to the cytoplasm in uninfected cells like wild-type protein V. Likewise, the fusions of pre-mu-EGFP and pre-VII-EGFP also localize to the nucleus and nucleolus in uninfected cells. A number of novel cellular and viral functions of these two core proteins have been revealed when expressed with the EGFP fusion (D. Matthews, personal communication). Based on these localization and conservation of function data in uninfected cells along with their ample copy numbers, these three core fusion proteins with EGFP represent promising strategies to genetically label adenovirus.

Noninvasive Optical Imaging for Detection of Molecular Targets

The discovery of photoproteins and fluorescent probes, advancement in photon-detection technology, and progress in image processing have actualized the power to noninvasively visualize molecular and physiological events in vivo. At the forefront of molecular imaging is an entire field devoted to optical imaging, involving the detection of light interaction with tissue based on "internal contrast" or more recently the visualization of biological probes with fluorescent and bioluminescent properties (Weissleder and Ntziachristos, 2003). Several groups have utilized green fluorescent protein (GFP) to detect tumor growth and metastases on a whole-body level without the need for substrate administration (Yang et al., 2000a; Hoffman, 2001). This method can provide readouts of fluorescence intensity that correlates with both tumor volume and weight, allowing noninvasive monitoring of tumor treatment (Diehn et al., 2002). In the same manner, gene expression can also be visualized on a whole-body scale (Yang et al., 2000b).

Although the tissue penetration for GFP detection is limited to 1–2 mm in experimental animals, there are some possible solutions. Recently identified novel fluorescent proteins with far-red or near infrared spectral properties, such as DsRed (Gross et al., 2000; Bevis and Glick, 2002), HcRed (Gurskaya et al., 2001), and monomeric red fluorescent protein (RFP) or tandem red fluorescent protein (Campbell et al., 2002) would give deeper signal tissue penetration.

Additionally, *Renilla* luciferase (Rluc) bioluminescence imaging has been established to detect both gene expression and tumor growth with great sensitivities (Bhaumik and Gambhir, 2002) and the potential of 3 cm tissue penetration (Weissleder and Ntziachristos, 2003). For signal production, Rluc only needs oxygen and its coelenterazine substrate which can be administered as low as 0.7 mg/kg body weight or roughly 100 µg per mouse. In contrast, firefly lucifersae requires ATP, $Mg^{2+}$, and other cofactors as well as its D-luciferin substrate which has to be given at 150 mg/kg body weight or about 3 mg per mouse. Additionally, Rluc is only a 36 kDa monomeric enzyme of roughly 900 bp size which has been used in both C-terminal and N-terminal fusions (Wang et al., 2002; Burbelo et al., 2002). Because it is very close in size to EGFP, it is believed that fusing it as a reporter to viral structural proteins proposed herein would provide a very promising alternative for highly sensitive detection of adenoviral replication and spread with deeper tissue penetration.

Moreover, data presented herein indicate that pIX-EGFP labeling of adenovirus was successful and that chimeric viruses labeled with pV-EGFP and pVII-EGFP also look promising. Thus, combination of capsid labeling along with core labeling to achieve "double labeling" is expected to yield more fusion protein signal and more intensely labeled viral particles. This double labeling strategy would be considered to achieve stronger signals for better noninvasive detection.

On the detection side, an imaging innovation called fluorescence molecular tomography (FMT) shows promise of localizing and quantifying fluorochromes three-dimensionally in deep tissues (7–14 cm) at high sensitivities (Weissleder and Ntziachristos, 2003). Additionally, the adaptation of clinically available imaging technologies, such as bronchoscopy, endoscopy, and laparoscopy, for intravital fluorescence imaging would give better access to targets and circumvent tissue depth issues. Several of these methods have already been successfully accomplished for fluorescence imaging of gene expression in rat brain (Ilyin et al., 2001) and in airway epithelia of monkeys (Rooney et al., 2002). These techniques can be simulated in mouse models by using a reversible skin flap technique to image brain, lung, and peritoneal tumors (Yang et al., 2002). Using such a method, one of skill in the art would be able to dynamically image replication and spread of labeled adenoviruses disclosed herein with greater sensitivity in an intraperitoneal tumor due to more direct access to the tumor.

In summary, one aspect of the present invention is to provide a method of monitoring the replication and distribution of adenoviral vectors in an animal or a human. The method involves first constructing adenoviral vectors that express a fusion protein comprising an adenoviral structural protein and a fluorescent tag. After administering these labeled adenoviral vectors to the subject, the level of viral replication and localization of these vectors in vivo can be determined by imaging the fluorescence of these viral agents. Preferably, adenoviral structural proteins suitable for fluorescent labeling include capsid protein pIX, core protein mu, core protein V or core protein VII. In general, the fluorescent tag can be enhanced green fluorescent protein, green fluorescent protein, *Discosoma* red fluorescent protein, far-red fluorescent protein, monomeric red fluorescent protein or *Renilla* luciferase. One of skill in the art would readily utilize a combination of imaging techniques to detect and measure the fluorescence of these viral agents. Representative imaging techniques include whole body fluorescence imaging, bronchoscopy, endoscopy and laparoscopy.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney, ed. 1986); "Immobilized Cells And Enzymes" (IRL Press, 1986); B. Perbal, "A Practical Guide To Molecular Cloning" (1984).

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1
Genetic Modification of Adenovirus Capsid Protein IIIa

Being adenovirus capsid proteins, pIIIa and pIX may be used as a carrier of heterologous peptide sequences, which may serve as purification tags or targeting ligands and, therefore, be utilized for virus purification or/and targeting. For the initial proof of concept, a six-His tag was incorporated into the amino-terminus of pIIIa, and a small 8-amino acid peptide tag—Flag (Asp Tyr Lys Asp Asp Asp Asp Lys, SEQ ID No. 1) was incorporated into the carboxy-terminus of pIX. The possibility to purify the modified viruses by binding to relevant affinity medium was demonstrated.

Construction of Recombinant Plasmids

In order to generate the shuttle vector for the modification of pIIIa gene, PmlI-fragment DNA (4055 bp) from plasmid pTG36021 containing complete Ad5 genome was cloned between SmaI and HincII sites in the plasmid pNEB193. Correct orientation of PmlI-fragment containing pIIIa gene in the context of pNEB193 was confirmed by restriction analysis and constructed plasmid was designated pNEBpIIIa (FIG. 1).

To introduce six histidine tag into the amino-terminal part of pIIIa protein, PCR was perform using PmlI-fragment DNA as a template and two pairs of primers: 1) pIIIaN.F: 5'-GCGAGGAGGTGGCTATAGG ACTGA (SEQ ID No. 2), pIIIaN6His.L: 5'-ATGGTGATGGTGATGGTGCATC TGATCAG AAACATC (SEQ ID No. 3); 2) pIIIaN.R: 5'-TTCGGCCAGCGCGTTTACGATC (SEQ ID No. 4), pIIIaN6His.U: 5'-CACCATCACCATCACCATATGCAAGACGCAAC (SEQ ID No. 5).

Primers pIIIaN6His.U and pIIIaN6His.L were designed to be partially complementary to the 5'-end of the pIIIa gene and to encode 6His. DNA products, 7440 and 261 bp, generated after first PCR were joined by second PCR using primers pIIIaN.F and pIIIaN.R, thereby generating DNA fragment (983 bp) corresponding for 5'-terminal portion of pIIIa gene with sequence coding for 6His introduced right after ATG codon.

Figure 2:
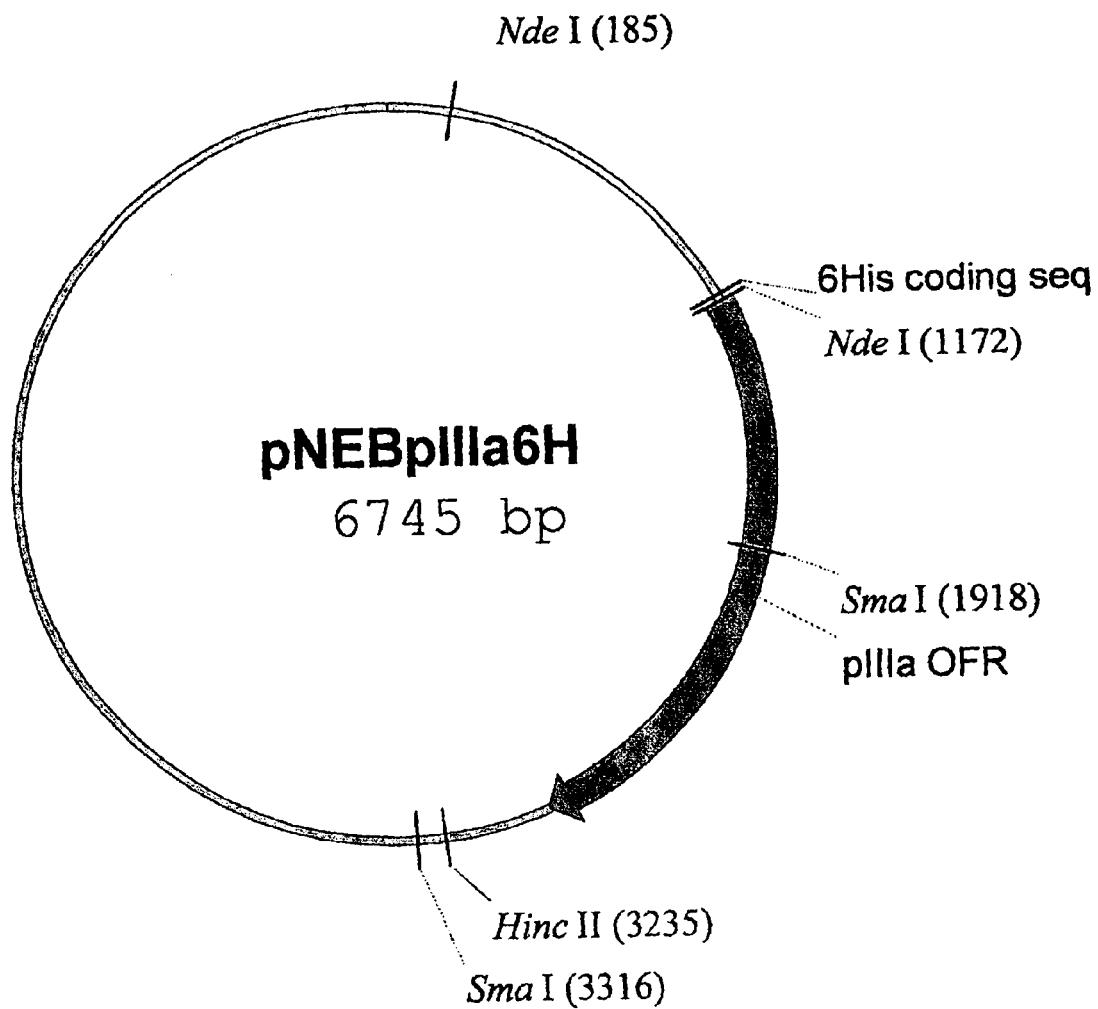
FIG. 2 shows the diagram of plasmid pNEBpIIIa6H.

To insert the modified part of the gene into the shuttle vector, pNEBpIIIa was digested with MluI and BsmI, the vector part was purified and then ligated with corresponding MluI-BsmI-fragment (738 bp) of PCR product. After transformation of *E. coli* with ligation mix, plasmid clones were analyzed for presence of MluI-BsmI-fragment. Confirmation for the correct structure of cloned PCR-originated DNA sequence coding for 6His tag was done by sequence analysis. Plasmid containing correct 6His-coding sequence was designated pNEBpIIIa6H (FIG. 2) and used as a shuttle vector to introduce the modification into Ad5 genome.

Figure 3:
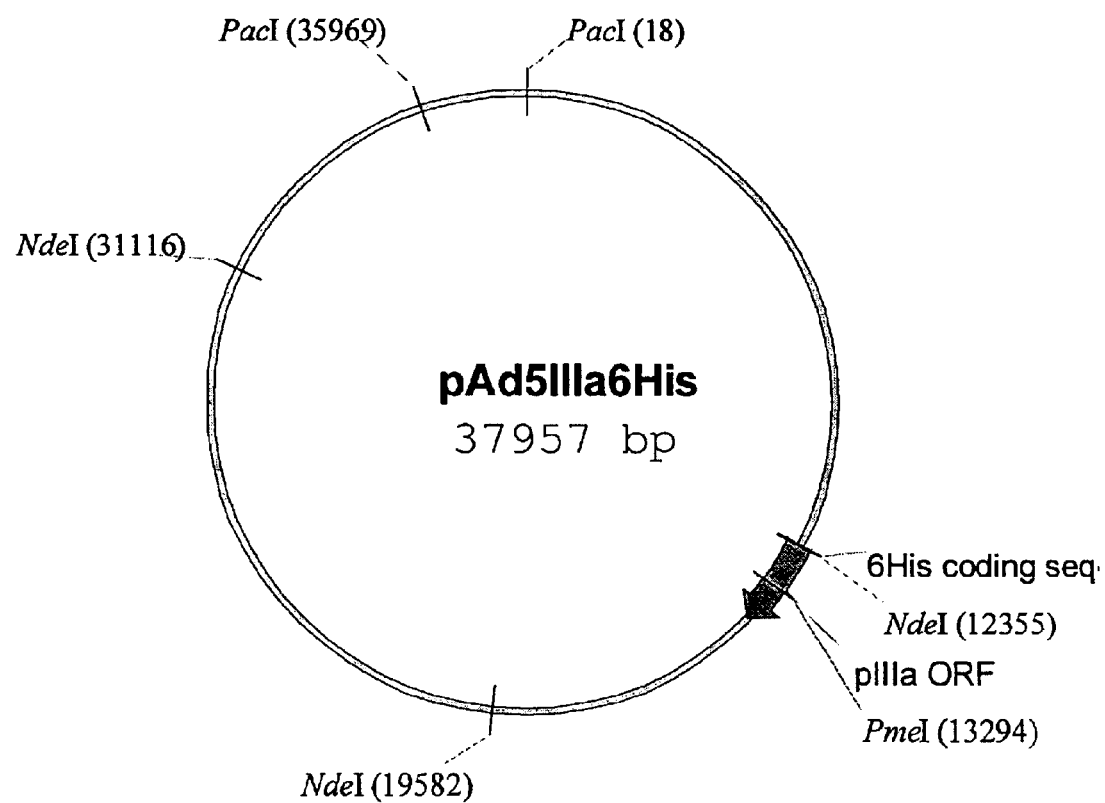
FIG. 3 shows the diagram of plasmid pAd5IIIa6His.

In order to obtain Ad5 genome containing modified gene for pIIIa, the shuttle vector pNEBpIIIa6H was utilized for homologous DNA recombination in *Escherichia coli* BJ5183 with PmeI-digested plasmid DNA pTG36021 as previously described (Chartier et al., 1996). The plasmid obtained as the result of this recombination was designated pAd5IIIa6His (FIG. 3). Ad vector, Ad5IIIa6His, containing recombinant IIIa gene coding for N-terminal 6His tag was generated by transfection of 293 cells with PacI-digested pAd5IIIa6His by the method described previously (Chartier et al., 1996).

Confirmating Insertion of 6His Coding Sequence in Ad Vector Genome

Figure 4:
FIG. 4 shows the appearance of a 260 bp DNA fragment after PCR indicating the presence of 6His coding sequence in the pIIIa gene of the modified Ad genome.

PCR was employed to demonstrate the presence of 6His coding sequence in pIIIa gene of the Ad genome. Sense primer N6His.U (5'-ATG CAC CAT CAC CAT CAC CAT ATG, SEQ ID No. 6) was design to be complementary to 6His coding sequence. Primer pIIIaN.R (5'-TTC GGC CAG CGC GTT TAC GAT C, SEQ ID No. 4) complementary to the sequence 260 bp downstream of 5'-end of pIIIa gene was used as antisense primer. The lyzate of 293 cell monolayer containing viral plaques 10 days posttrasfection was used as a template for PCR. Appearance of 260 bp DNA fragment after PCR (FIG. 4) indicates the presence of 6His coding sequence in the pIIIa gene of the modified Ad genome.

EXAMPLE 2

Genetic Modification of Adenoviral Capsid Protein IX

Figure 5:
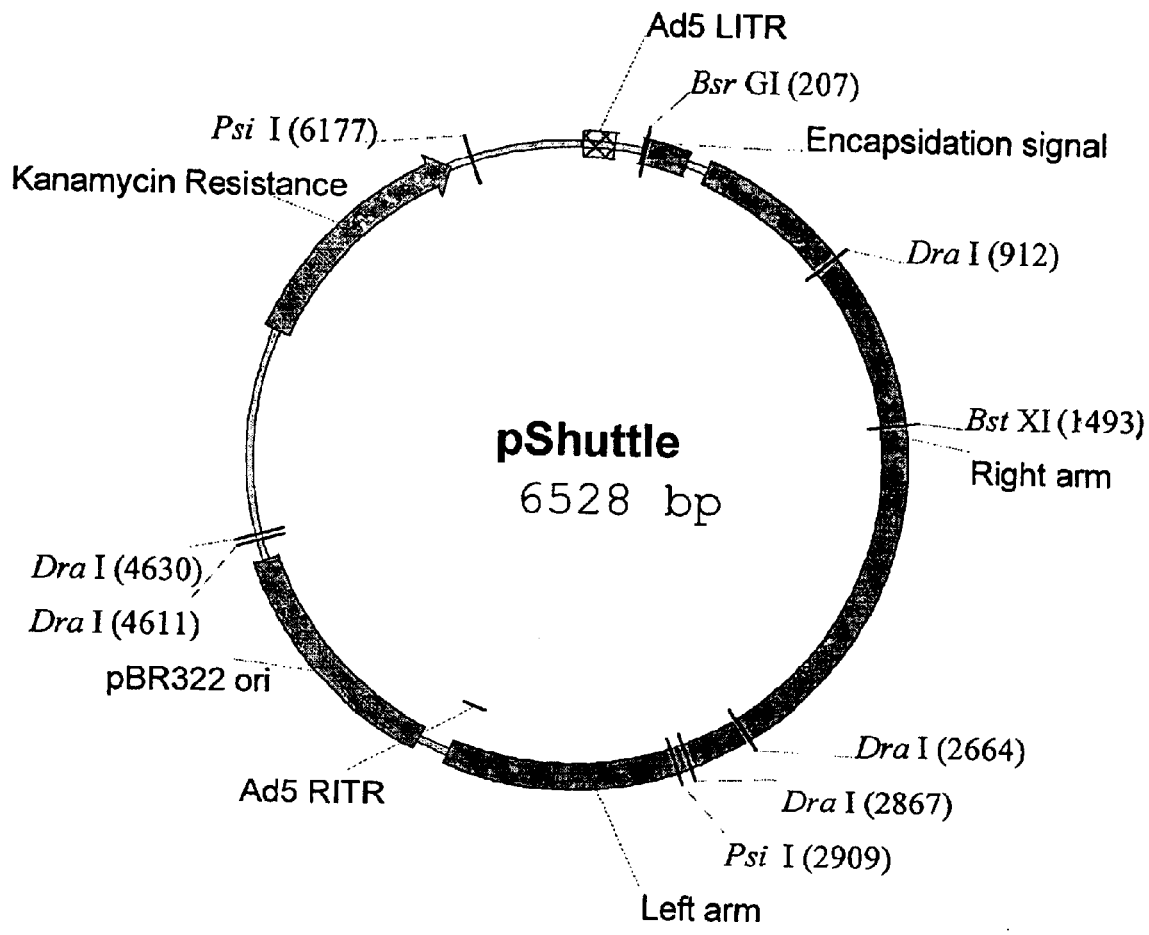
FIG. 5 shows the diagram of plasmid pShuttle.

In order to generate the shuttle vector for incorporation of Flag peptide (Asp Tyr Lys Asp Asp Asp Asp Lys, SEQ ID No. 1) into the C-terminus of the IX protein, AdEasy vector system was utilized (He et al., 1998). Oligonucleotides FLAGc.U: 5'-CTG CCG ATT ATA AGG ATG ACG ATG ACA AGT (SEQ ID No. 7) and FLAGc.L: 5'-ACT TGT CAT CGT CAT CCT TAT AAT CGG CAG (SEQ ID No. 8) were designed to form DNA duplex coding for Flag peptide. DNA duplex was cloned into DraI site located at 3'-end of pIX coding sequence. Cloning of the Flag oligo was done by ligation of BsrGI-DraI and DraI-BstXI fragments of DNA isolated from pShuttle plasmid (FIG. 5) with oligo duplex and subsequent cloning of the resultant DNA fragment between BsrGI and BstXI sites in pShuttle plasmid. After transformation of *E. coli* with ligation mix, plasmid clones were analyzed for the presence of Flag-oligo insert by PCR using upper primer designed for the position of 3904 in Ad5 genome (5'-AGT TGA CGG CTC TTT TGG CAC A, SEQ ID No. 9) and FLAGcL as lower primer. PCR-positive clone was then analyzed for the presence of Psi I site, designed inside of the Flag-oligo, by digestion with Psi I.

Figure 6:
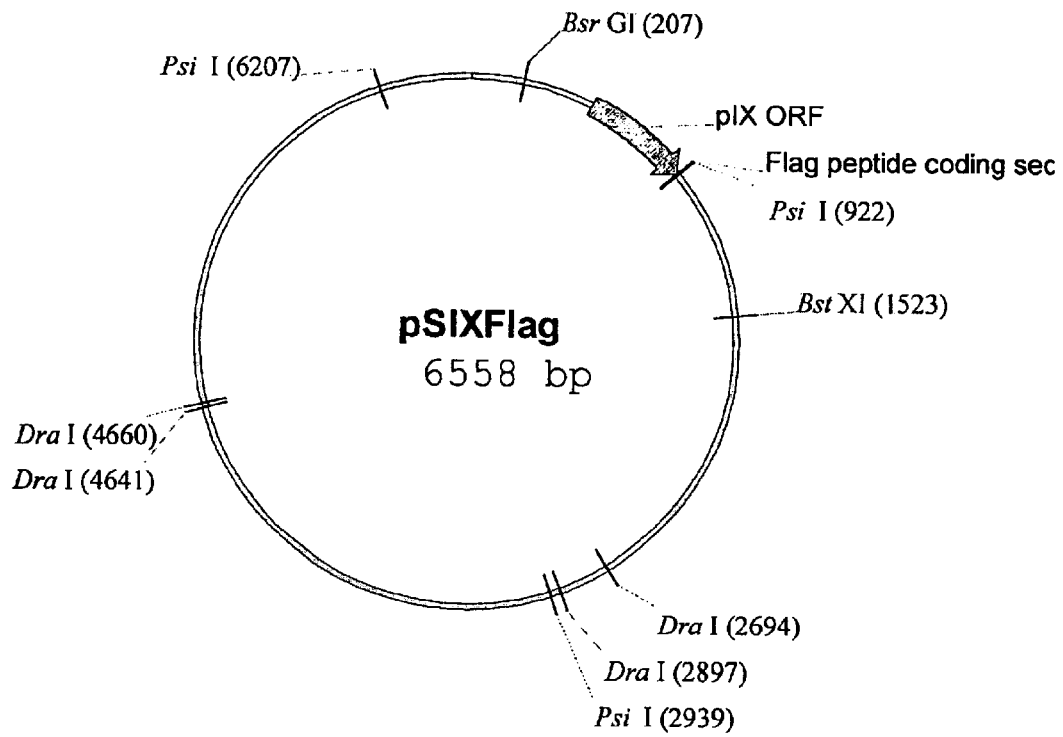
FIG. 6 shows the diagram of plasmid pSIXFlag.
Figure 7:
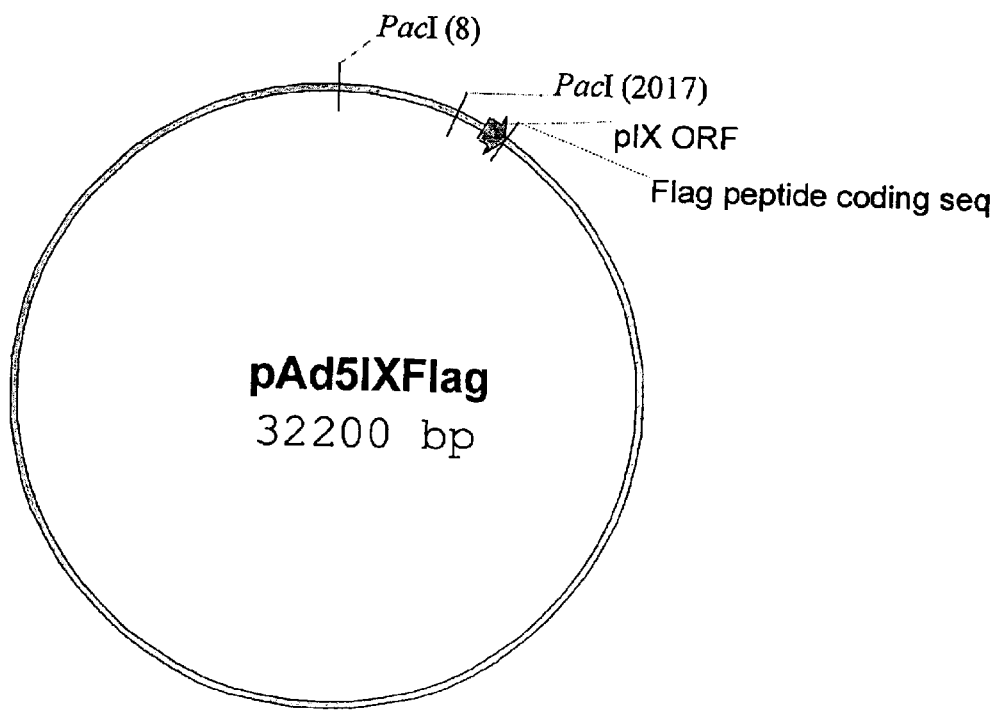
FIG. 7 shows the diagram of plasmid pAd5IXFlag.

After sequence analysis of the correct structure of Flag-oligo cloned into 3'-end of pIX gene the resultant plasmid, pSIXFlag (FIG. 6), was utilized for homologous DNA recombination in *Escherichia coli* BJ5183 with plasmid DNA pAdEazyl containing Ad genome as described (He et al., 1998). The plasmid obtained as the result of this recombination was designated pAd5IXFlag (FIG. 7) and was used to generate Ad vector containing recombinant IX gene coding for C-terminal Flag peptide. Ad vector, Ad51XFlag, was generated by transfection of 293 cells with PacI-digested pAd5IXFlag by the method described previously (He et al., 1998).

Confirmating the Presence of Flag Peptide in the Adenoviral Capsid

Figure 8:
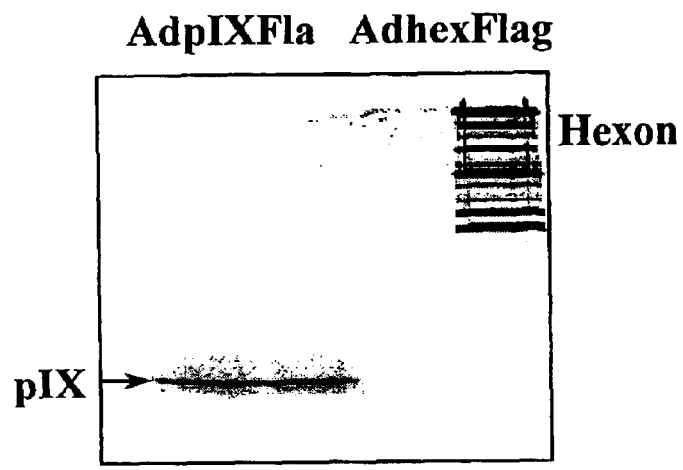
FIG. 8 shows western blot analysis of Ad vector containing the Flag peptide tag in the IX capsid protein. Viral capsomers from AdpIXFlag or Ad5hexFlag that contains Flag peptide in hexon protein were separated by electrophoresis, transferred onto PVDF membrane and incubated with anti-Flag M2 MAb followed by incubation with secondary anti-mouse Ab conjugated with alkaline phosphatase. The presence of protein band of 15 kDa corresponds to the expected molecular weight of protein IX containing Flag peptide.

In order to characterize generated Ad vector for the presence of Flag peptide containing protein IX in the viral capsid, Western blot analysis was done. Virus purified on CsCl gradient was boiled in Lemmli buffer and loaded on SDS-PAGE gel to separate the proteins of viral capsid. Ad vector, Ad5hexFlag, containing Flag peptide in hexon protein was used as a positive control for the Western blot. Viral capsomers separated during electrophoresis were transferred onto PVDF membrane and incubated with anti-Flag M2 MAb followed by incubation with secondary anti-mouse Ab conjugated with alkaline phosphatase. Western blot analysis revealed the presence of protein band of 15 kDa that corresponds to the expected molecular weight of protein IX containing Flag peptide (FIG. 8).

Figure 9:
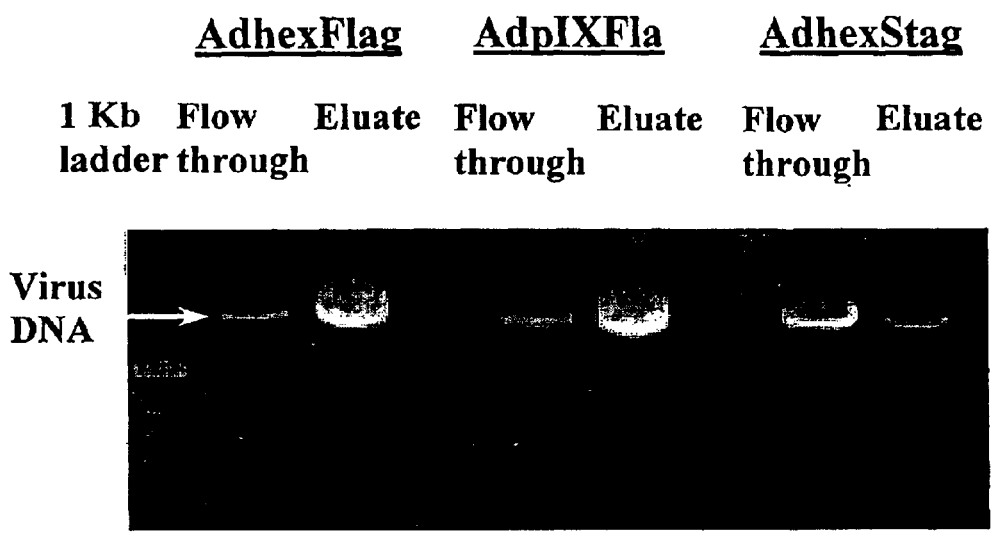
FIG. 9 shows the surface localization of Flag peptide in the context of assembled viral capsid protein IX. Flow through or eluates that bind to an affinity column containing anti-Flag M2 Mab were lyzed by lysis buffer and loaded onto agarose gel in order to visualize viral DNA. Major bands of high molecular viral DNA was visualized in the eluate fractions of Ad5IXFlag and that of positive control AdhexFlag, whereas major amount of viral DNA was found in the flow through fraction of the negative control Adhex-Stag.

To demonstrate the surface localization of Flag peptide in the context of assembled viral capsid of the generated virus, affinity column purification was performed. Ad vectors containing accessible Flag and StrepTag peptides in hexon protein were used respectively as a positive and a negative control for purification. CsCl-purified virus was loaded onto the column containing anti-Flag M2 MAb agarose beads and the column was then washed to remove unbound virus. Virus bound to column was lyzed by incubation of agarose beads with viral lyses buffer (0.6% SDS; 10 mM EDTA; 100 $\mu$g/ml Proteinase K) for 10 min. at 56° C. in order to release viral DNA from virions. Virions that passed through the column without binding to M2 MAb (flow through) were lyzed by incubation with lyses buffer as well. Aliquots of flow through and eluate fractions collected throughout the purification of generated Ad5IXFlag as well as the control viruses were loaded onto agarose gel in order to visualize viral DNA. DNA electrophoresis revealed the presence of major bands of high molecular viral DNA in eluate fractions of Ad5IXFlag and positive control virus (FIG. 9). In case of negative control virus containing StrepTag peptide the major amount of viral DNA was found in flow through fraction. These data strongly indicate that Flag peptide incorporated into C terminus of IX protein is displayed on the outer surface of adenoviral capsid and accessible for binding interactions in the context of assembled viral particle.

EXAMPLE 3

Construction of EGEP-Labeled Capsid Protein pIX

The present example demonstrates the fusion of enhanced green fluorescent protein (EGFP) to the C-terminal of capsid protein pIX.

Figure 10A:
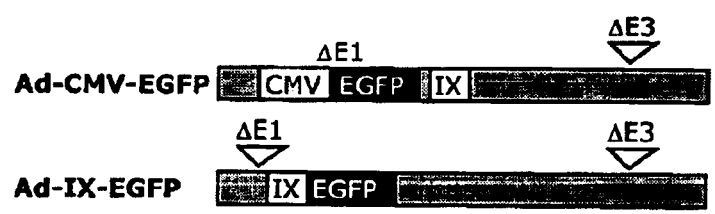
FIG. 10A shows control Ad-CMV-EGFP construct with native pIX and Ad-IX-EGFP construct with pIX-EGFP in place of native pIX.

All adenoviral constructs were generated by a shuttle vector/homologous recombination in *Escherichia coli* (He et al., 1998). Control virus Ad-CMV-EGFP expressed enhanced green fluorescent protein (EGFP, BD Biosciences, Clontech, Palo Alto, Calif.) in E1 and contained native IX. To construct Ad-IX-EGFP, the EGFP HincII-SacI fragment from pABS.4-CMV-tetR-EGFP was blunted with large Klenow fragment (New England Biolabs, Beverly, Mass.) and inserted in frame into pShuttle-NheI-FLAG (Dmitriev et al., 2002) which was linearized with NheI and blunted. A correct clone based on restriction digestion and expression of pIX-EGFP was linearized with PmeI and homologously recombined with pAdEasy-1 in electrocompetent BJ5183 to generate an adenoviral backbone containing IX-EGFP in place of wild-type IX. Both Ad-CMV-EGFP and Ad-IX-EGFP were E1- and E3-deleted (FIG. 10A).

A wild-type adenovirus with IX-EGFP was made as a surrogate model of replicative adenoviruses for both in vitro and in vivo replication studies in human cancer cell lines. The cloning strategy involved insertion of an SgrAI-MfeI fragment from pXC1 (Microbix, Toronto, Canada) containing the entire wild-type E1 region into pShuttle-IX-EGFP linearized with SgrAI and MfeI to generate pShuttle-wt-E1-IX-EGFP. The PacI fragment of this plasmid was reversed to match its original direction. A PmeI linear cut of this plasmid was then homologously recombined with pTG3602-AmpF2, an adenoviral backbone plasmid with an Amp gene 5' of the origin of replication and deletion in E1 to help with correct recombination. The final construct contained wild-type Ad5 sequences with IX-EGFP in place of native IX.

EXAMPLE 4
Propagation of Fluorescent-Labeled Viruses and Titering

The final viral backbones was linearized with PacI and then transiently transfected into 911 cells (Superfect, Qiagen, Valencia, Calif.) for virus propagation. Amplification involved the use of 911 cells in one 15 cm dish and then three dishes. 293 cells were used in the final amplification of 20 dishes for purification. For characterization studies, propagation was done in 10 dishes. Viruses were purified by double CsCl ultracentrifugation and dialyzed against phosphate-buffered saline with $Mg^{2+}$, $Ca^{2+}$, and 10% glycerol. Final aliquots of virus were analyzed for viral particle titer (optical density at 260 nm) and fluorescent cell unit titer (fcu). Fcu was determined by infecting 911 cells in 96-well plates with various dilutions of virus and counting the number of green cells 2 days post-infection (n=6). Viruses were stored at −80° C. until use.

EXAMPLE 5
Verification of pIX-EGFP Fusion Protein Expression and Localization

Conservation of cellular localization of the fusion protein label relative to the native structural protein is imperative because of consequences associated with function and likelihood of being packaged into virions. This issue is especially important when a transgene is expressed in an adenoviral context where viral factors or perturbations of the cellular environment due to infection may affect the localization and function of the protein.

Expression and localization of the structural fusion proteins were confirmed by infecting 911 cells and visualizing EGFP fluorescence from the fusion protein using an IX-70 microscope (Olympus, Melville, N.Y.) equipped with a Magnifire digital CCD camera (Optronics, Goleta, Calif.). Hoechst staining (Molecular Probes, Eugene, Oreg.) was used to visualize nuclear DNA and verify the nuclear localization of the fusion protein label.

Figure 10B:
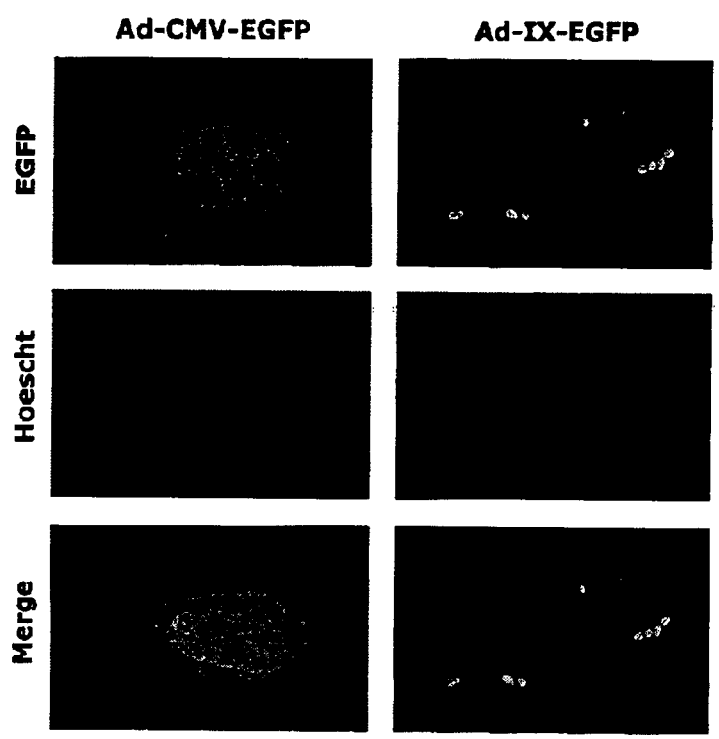
FIG. 10B shows EGFP localization from Ad-CMV-EGFP and pIX-EGFP nuclear localization from Ad-IX-EGFP.

An E1-deleted shuttle plasmid was constructed containing a IX-EGFP carboxy-terminal fusion gene in place of wild-type IX. Following transient transfection of this plasmid into 911 cells, pIX-EGFP was expressed and accumulated in intranuclear clear amorphous inclusions as previously reported (data not shown). This shuttle plasmid was used to construct E1- and E3-deleted Ad-IX-EGFP (FIG. 10A) which was successfully rescued. In an adenoviral context, pIX-EGFP was expressed and also accumulated in the nucleus (FIG. 10B).

EXAMPLE 6
Incorporation of pIX-EGFP Into Ad-IX-EGFP Particles

Double cesium chloride ultracentrifugation provides a way to clearly separate mature viruses from empty capsids in a gradient. This gradient was analyzed fraction by fraction to determine the success of protein label incorporation into virions. For these fractionation studies, the top and bottom bands were retained through both CsCl ultracentrifugation steps yielding one tube from ten 15 cm dishes. After the second spin, fractions of two drops each (~100 uL) were collected through a perforation created at the bottom of the tube and stored at 4° C. until use. Fluorescence of the fractions was measured with a Versafluor fluorometer (BioRad, Hercules, Calif.) using 490/10 nm excitation and 510/10 nm emission filters (Chroma Technology, Brattleboro, Vt.). Alternatively, fraction fluorescence can also be measured in a white opaque microplate using a BMG Labtechnologies Fluorostar microplate fluorometer (Durham, N.C.). DNA content of the same fractions was determined by measuring optical density at 260 nm (MBA 2000, Perkin Elmer, Shelton, Conn.).

Figure 11:
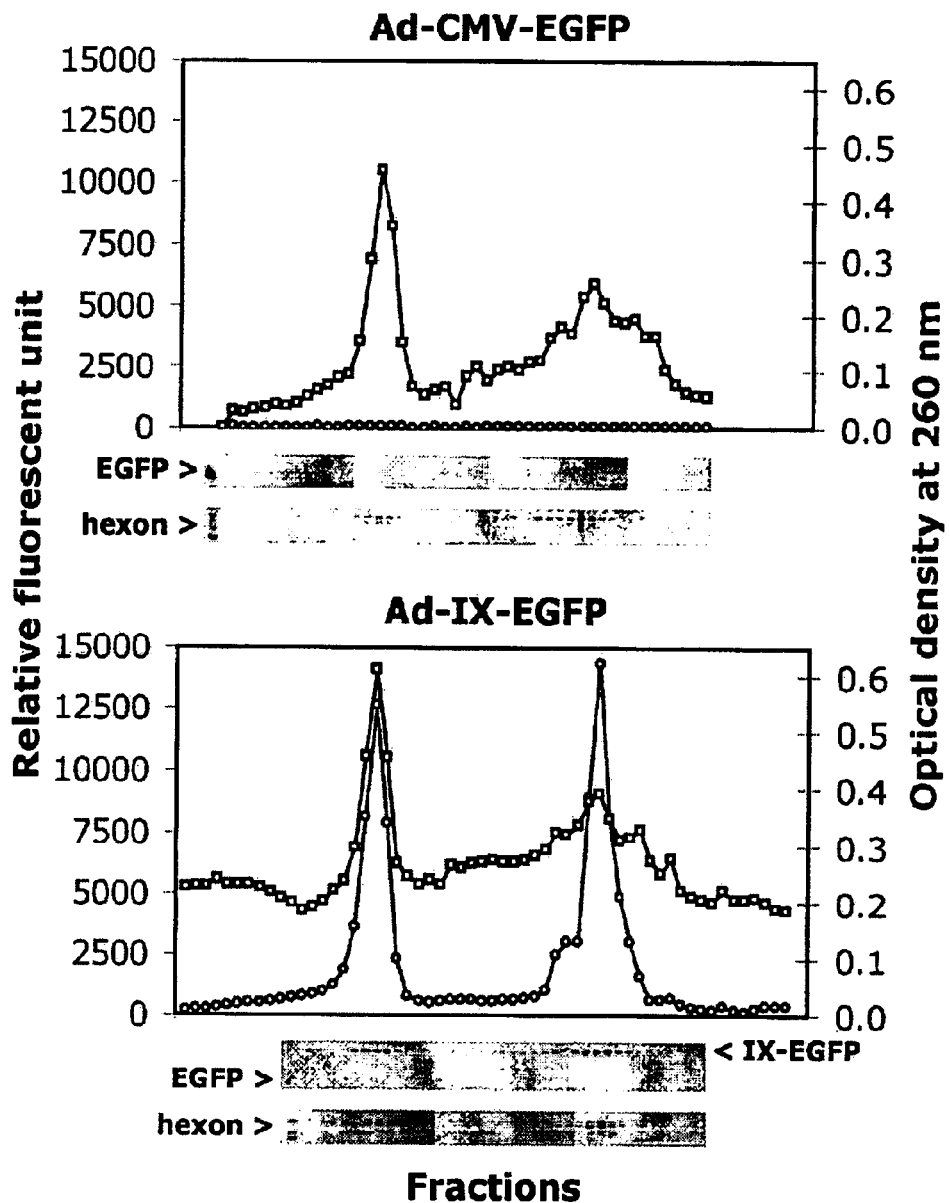
FIG. 11 shows characterization of Ad-IX-EGFP particles. Fluorescence (bottom line) and DNA content (upper line) of Ad-CMV-EGFP and Ad-IX-EGFP CsCl gradient fractions were shown after double ultracentrifugation. Fractions were also analyzed using anti-GFP and anti-hexon western blotting.

Fluorescent peaks were observed for the top and bottom band fractions of Ad-IX-EGFP which were significantly greater than those of control Ad-CMV-Luc (data not shown) and Ad-CMV-EGFP (more than 2 log factors). For all viruses, a major DNA content peak was present in the bottom band where mature virions normally migrate (FIG. 11). Infectious, mature Ad-IX-EGFP particles were present in the bottom band as indicated by an infectivity peak in a quick CPE assay (data not shown).

The same gradient fractions for Ad-IX-EGFP and Ad-CMV-EGFP were also analyzed with western blot using GFP and hexon antibodies. Fractionated samples (4 uL) were ethanol precipitated (final 95% ethanol concentration), pelleted, and resuspended with 20 uL RIPA buffer (1% sodium deoxycholate, 0.1% SDS, 1% Triton X-100, 1% bovine hemoglobin, 1 mM iodoacetamide, aprotinin (0.2 trypsin inhibitor U/mL), 1 mM phenylmethylsulfonyl fluoride, 0.002 M Tris.Cl (pH 8.0, 4° C.), 0.14 M NaCl, 0.025% $NaN_3$). Samples (5 uL) were resolved with SDS-PAGE and then transferred to a PVDF membrane (BioRad, Hercules, Calif.). Blotting was performed with a primary monoclonal anti-GFP antibody (1:1000 dilution, BD Biosciences Clontech) followed by a secondary HRP-linked mouse antibody (1:5000 dilution, Amersham Pharmacia, Piscataway, N.J.) or a primary polyclonal anti-hexon antibody (1:1000 dilution, Chemicon International, Inc., Temecula, Calif.) followed by a secondary HRP-linked goat antibody (1:5000 dilution, Dako, Carpinteria, Calif.). Bands were detected with a chemiluminescent BCL kit (Amersham Pharmacia). Colocalization of core fusion protein signal with that of hexon would verify incorporation of the label into virions.

The blots showed accumulations of pIX-EGFP and hexon in both the top and bottom band regions for Ad-IX-EGFP, confirming the colocalization of pIX-EGFP with the capsid and hence virions. While hexon was also detected both in the bottom and top bands for Ad-CMV-EGFP, EGFP was only present above the top band where cellular proteins migrate (FIG. 11). These data validate successful labeling of adenovirus with pIX-EGFP.

Figure 12:
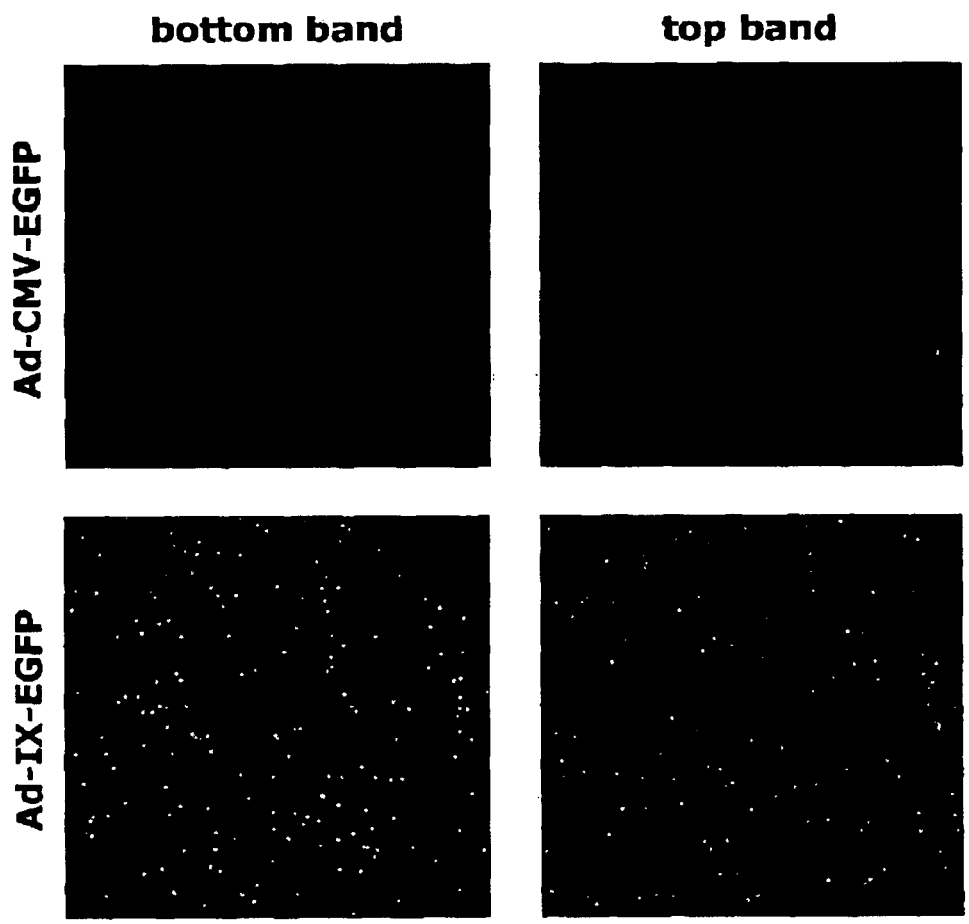
FIG. 12 shows visualization of Ad-IX-EGFP particles. Dilutions (1:100) of representative top and bottom band fractions for Ad-CMV-EGFP and Ad-IX-EGFP were visualized with epifluorescence microscopy using a 100× oil immersion objective.

Whether or not the extent of labeling confers actual detectability of viral particles was assessed by fluorescence microscopy. Labeled viral particles were examined with epifluorescence microscopy using an IX-70 microscope (Olympus, Melville, N.Y.) equipped with a Magnifire digital CCD camera (Optronics, Goleta, Calif.). Images were acquired with a 100× oil immersion objective and processed with Adobe Photoshop 6.0 (San Jose, Calif.). As shown in FIG. 12, Ad-IX-EGFP bottom and top band fractions revealed abundant punctate green particles. The fluorescence of bottom band mature particles was uniform whereas the fluorescence of top band empty particles had variable intensities. No fluorescent particles were detected for control Ad-CMV-Luc (data not shown) or Ad-CMV-EGFP (FIG. 12).

EXAMPLE 7
Detection of Ad-IX-EGFP Binding

Figure 13:
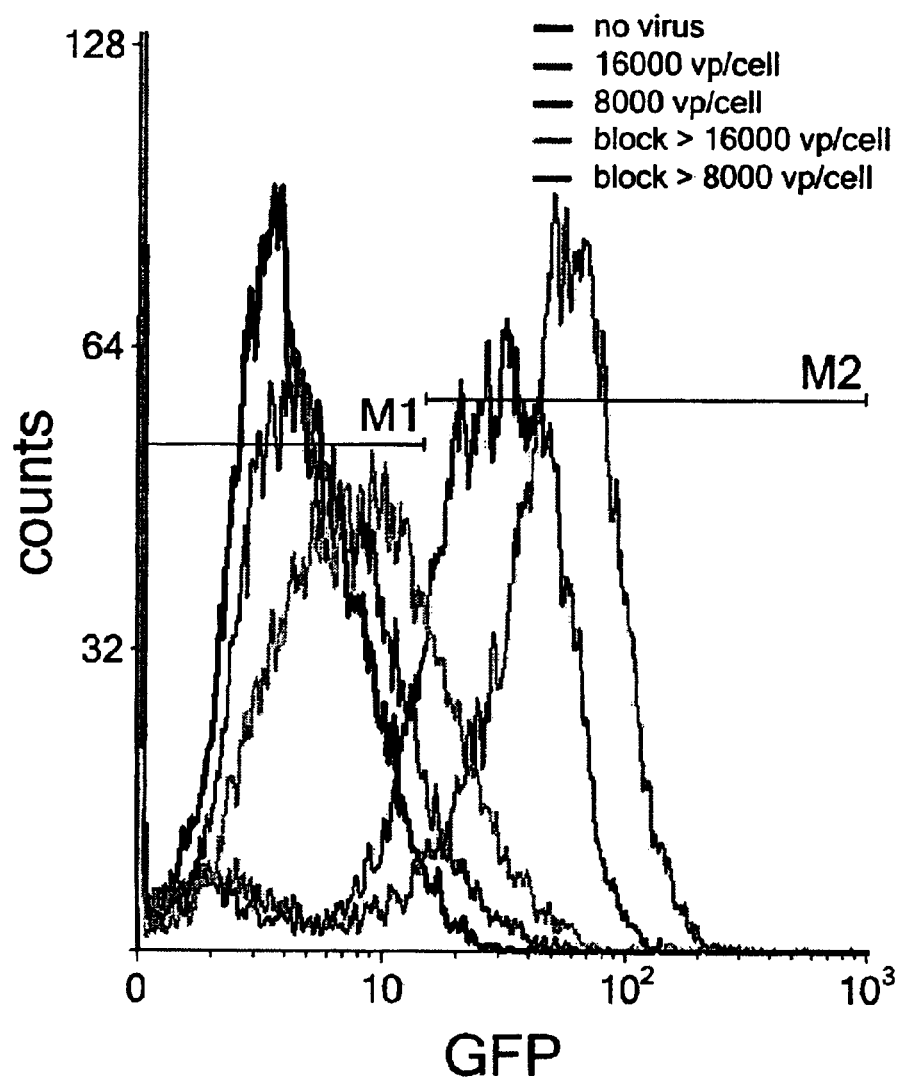
FIG. 13 shows Ad-IX-EGFP FACS binding assay. 911 cells (positive for primary adenovirus receptor) were incubated, with (gray) or without (green) Ad5 knob before addition of virus. After the virus was allowed to bind, the cells were analyzed by FACS to detect cells positive for bound virus. Black line represents control cells incubated without knob protein block and without virus.

Ad-IX-EGFP detection in a functional context was demonstrated by exploiting the fluorescent property of this virus to assay its binding to cells. 911 cells which express the coxsackieadenovirus receptor (CAR) were first incubated with or without a recombinant adenovirus type 5 fiber-knob protein, followed by incubation with Ad-IX-EGFP for 30 minutes at 4° C. (with shaking). The cells were then washed and analyzed by FACS for any bound EGFP signal. Without prior blocking, Ad-IX-EGFP binding to 911 cells clearly showed positive peaks at 16000 viral particles/cell and 8000 viral particles cell compared to the uninfected control. However, incubation with the fiber-knob protein before addition of virus blocked subsequent binding of Ad-IX-EGFP to its primary receptor CAR at the same multiplicities of infection (FIG. 13). These results indicate the detectability of Ad-IX-EGFP for binding activity and pIX-EGFP labeling did not have a deleterious effect on the binding of virus.

EXAMPLE 8
Tracking of Ad-IX-EGFP Infection

In addition to binding, any modification of virus capsid could affect its infection pathway. Hence, a tracking assay was used to monitor the infection of Ad-IX-EGFP in 911 cells, again exploiting the fluorescent property of the virus for its detection. 911 cells were plated on glass bottom plates (World Precision Instruments, Sarasosta, Fla.) the day prior to infection. After Hoechst nuclear counter-staining, infection was performed between 100 to 1000 vp/cell. Because monitoring of infection was done at room temperature and in ambient air, HEPES buffer was added to the medium (final concentration 25 mM) to maintain physiological pH. Image acquisition was accomplished as described above.

Figure 14:
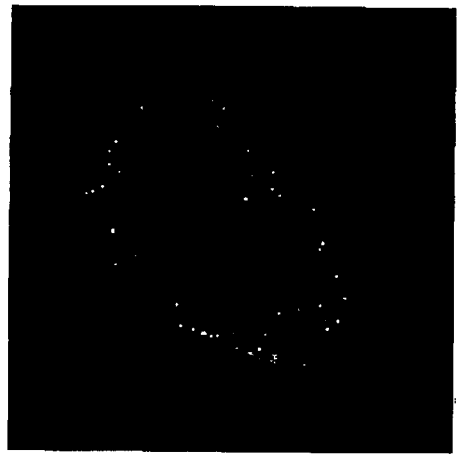
FIG. 14 shows tracking of Ad-IX-EGFP infection of 911 cells. Top two panels show binding of virus on the cell membrane at ~30 minutes after infection at room temperature. Bottom two panels show accumulation of virus around the nucleus ~1–2 hours after infection at room temperature. Blue represents Hoechst stain for the nucleus.
Figure 14:
Figure 14:
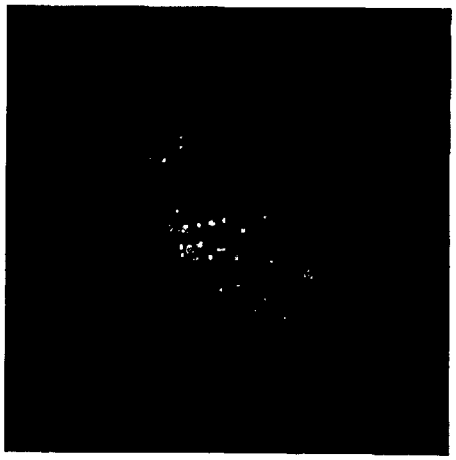
Figure 14:
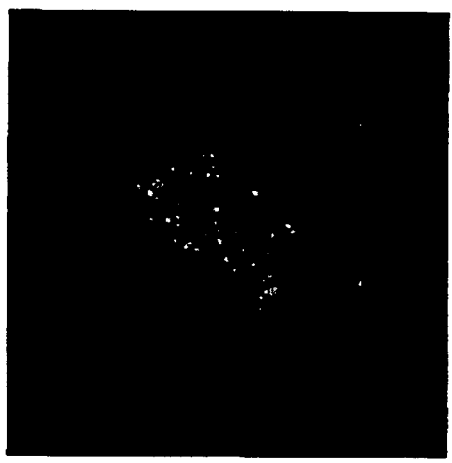

As shown in FIG. 14, shortly after addition of the virus to the culture medium (30 min), numerous viral particles were observed binding on the cell membrane periphery. After another hour at room temperature, viruses were detected mostly in the nucleus (FIG. 14). Evidently, the pIX-EGFP label did not affect the infectivity of the labeled adenoviruses.

EXAMPLE 9
DNA Packaging Efficiency of Ad-TX-EGFP

With successful labeling, detection, and confirmation of binding and infectivity for Ad-IX-EGFP established, the adaptability of this labeling strategy for a replicative system was next evaluated. Ideally for application in replicative adenoviral vectors, pIX-EGFP labeling of adenovirus should minimally disrupt the efficiency of viral replication and virus production. Although dispensible in packaging, adenovirus pIX is important in packaging full-length genomes and stabilizing the capsid structure. One way to measure the effectiveness of replication and progeny production is to determine the efficiency of DNA encapsidation. 911 cells ($5\times10^4$) were infected with control or fluorescently labeled viruses at 10 fluorescent cell units/cell in 12-well plates. On days 1, 2, 3, and 4 post-infection, the cells and medium were collected, processed for DNA, and analyzed with quantitative Taqman PCR (LightCycler™ System, Roche Applied Science, Indianapolis, Ind.) as previously described (Yamamoto et al.) Briefly, one half of the cell pellet was processed for total intracellular DNA (viral and genomic) using a DNA Blood Mini Kit (Qiagen, Valencia, Calif.). The second half was assayed for intracellular viral DNA by first lysing the cells with a non-detergent buffer containing sodium deoxycholate. This process disrupted the cell membrane to release intact viral particles. Unencapsidated viral DNA and free genomic DNA were degraded with DNAse and then precipitated with spermidine. Isolation of encapsidated viral DNA was then done with the DNA Blood Mini Kit. In a similar manner, the supernatant was processed for released encapsidated viral DNA using DNAse and spermidine method. Viral DNA quantitation was performed with E4 specific primers.

Figure 15:
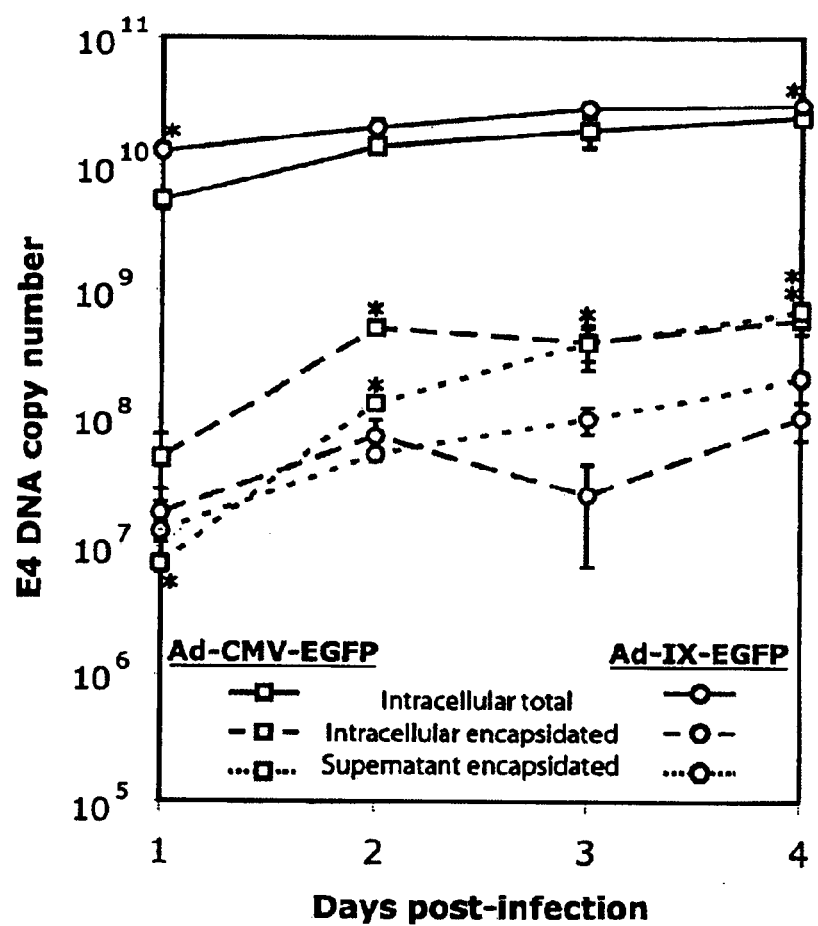
FIG. 15 shows DNA packaging efficiency and progeny production of Ad-IX-EGFP. The results shows post-infection copy numbers of viral DNA from various pools for Ad-CMV-EGFP and Ad-IX-EGFP (n=3). * DNA copy numbers were statistically different (t-test $P<0.05$) between the two viruses in the following cases: total intracellular DNA on days 1 and 4; intracellular encapsidated DNA on days 2, 3, and 4; and superanatant encapsidated DNA on days 1, 2, and 4.

As shown in FIG. 15, total viral DNA replication was the same for both Ad-IX-EGFP and control Ad-CMV-EGFP. However, both packaged DNA in the cell and packaged DNA released into the supernatant was approximately half a log factor lower for Ad-IX-EGFP compared to the control (FIG. 15), indicating lower progeny yield. This effect was significant, yet the yield of Ad-IX-EGFP was on the same order of magnitude as the control Ad-CMV-EGFP.

EXAMPLE 10
Cytopathic Effect of Ad-IX-EGFP

Figure 16:
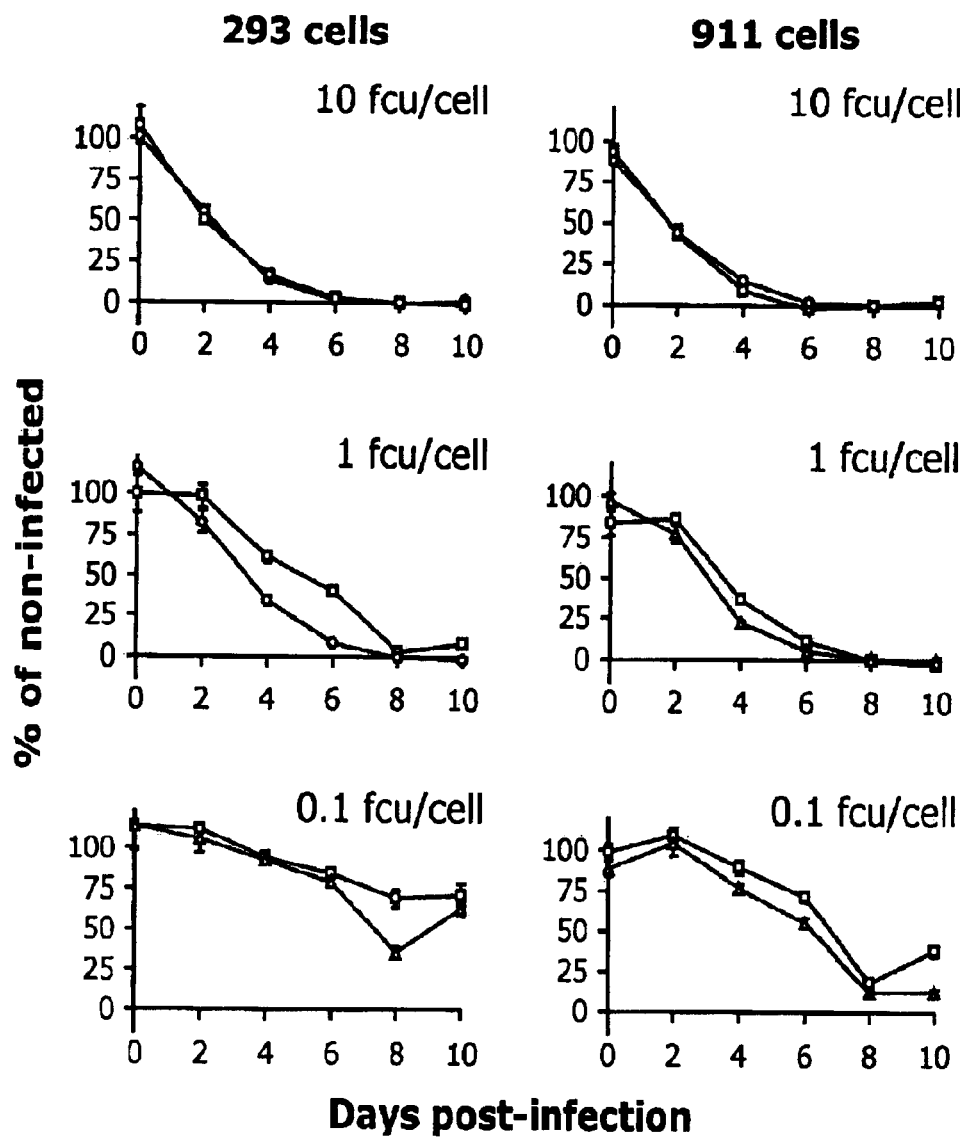
FIG. 16 shows cytopathic effect and spread of Ad-IX-EGFP. Cytopathic effect of Ad-CMV-EGFP (squares) and Ad-IX-EGFP (triangles) in 293 cells (complementary pIX expression) and 911 cells (no pIX expression) at various multiplicities of infection. Cytotoxicity measured by a non-radioactive proliferation assay and expressed as percentage of non-infected cells (n=6).

In addition to efficiency of progeny production, the efficacy of replicative adenoviruses also depends on how well the virus can lyse infected tumor cells and spread leading to an overall cytopathic effect. To evaluate cytopathic effect quantitatively, infection of 911 and 293 cells with Ad-IX-EGFP or control virus at 10, 1, and 0.1 fcu/cell multiplicities of infection (moi) were monitored over 10 days. On days 0, 2, 4, 6, 8, and 10, the cytopathic effect of the virus was quantitated using a non-radioactive cell proliferation assay (MTS assay) (FIG. 16). Both 293 and 911 packaging cell lines for E1-deleted adenoviruses have been shown to express very low levels of wild-type pIX. In both 293 and 911 cells, the cytopathic effect of Ad-IX-EGFP was the same as that of Ad-CMV-EGFP. These findings suggest that although Ad-IX-EGFP has a slightly lower yield than control virus, pIX-EGFP did not affect the cytopathic capacity and lateralization of the virus that are critical functions of replicative adenoviral agents.

Figure 17:
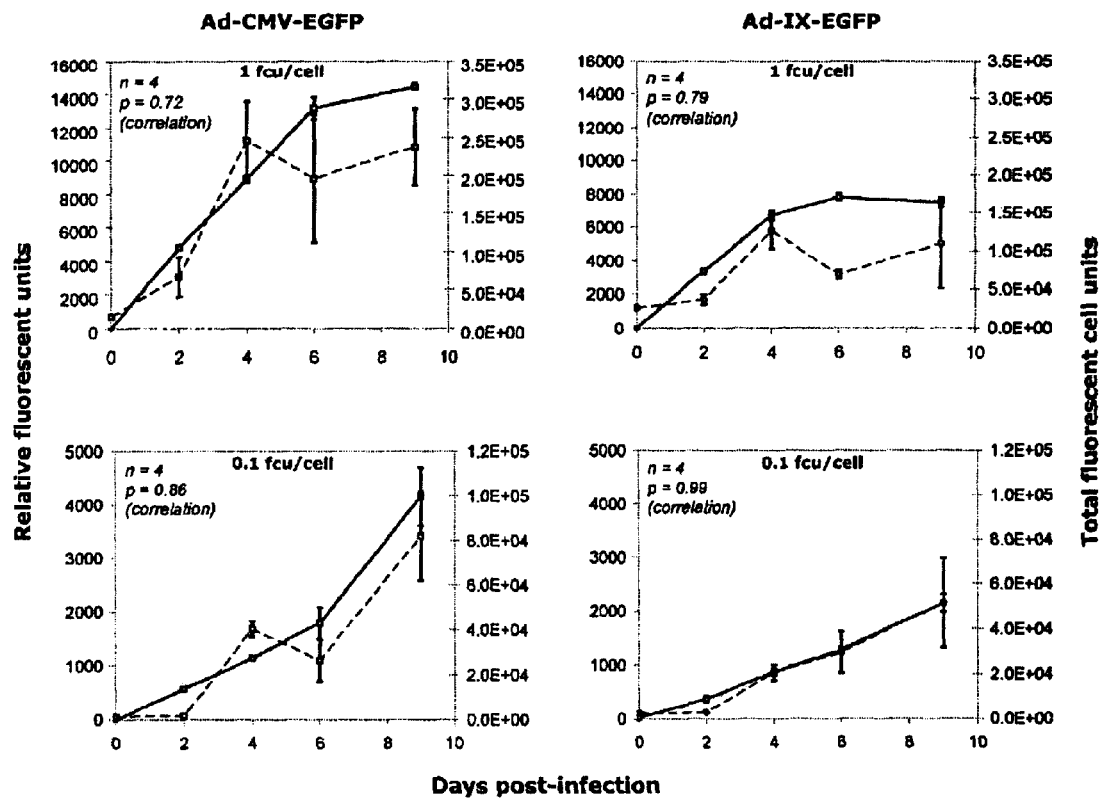
FIG. 17 shows correlation of fluorescent protein label with progeny production. 911 cells were infected with control Ad-CMV-EGFP or Ad-IX-EGFP at 1 and 0.1 fcu/cell. On days 0, 2, 4, 6, 8, and 9 post-infection, the fluorescence of the cells (solid lines) was measured and correlated with the titer of crude viral lysate (dotted lines) prepared from the same samples.

EXAMPLE 11
Correlation of pIX-EGFP Fluorescent Label with Replication and Progeny Production In addition to localizing the spread of progeny virions, the power of a monitoring system for replicative agents also depends on its ability to accurately represent the level of viral replication and progeny production. Whether the pIX-EGFP labeling approach satisfy this criterion was examined as follows. 911 packaging cells were infected with Ad-IX-EGFP or control Ad-CMV-EGFP (both E1- and E3-deleted) at 1 and 0.1 fcu/cell. On days 0, 2, 4, 6, 8, and 9 post-infection, the fluorescence of pIX-EGFP and EGFP in the cells were quantitated. Cells and culture medium were collected on these days and lysed with three freeze/thaw cycles. The crude viral lysates from these samples were titered in terms of fluorescent cell units. The time-course fluorescence and progeny production based on fluorescent cell unit titer were plotted together to show the degree of correlation between the two measurements (FIG. 17). Correlation p values were calculated by taking the covariance between the fluorescence and fluorescent cell unit titer data sets (means only) and dividing it by the product of the variances of the two data sets (means only). At the lower moi, the correlation of pIX-EGFP fluorescence with fluorescent cell unit titer for Ad-IX-EGFP was much stronger than that of Ad-CMV-EGFP ($p=0.99$ vs. $p=0.86$, respectively) (FIG. 17). At the higher moi, both systems appear to be saturated with progeny virus by day 4 leading to a drop in titer on the following days. These data indicate that the fluorescence of the pIX-EGFP label can be used to represent the level of replication and progeny production.

EXAMPLE 12
Dependence of pIX-EGFP Expression on Viral Replication

Figure 18:
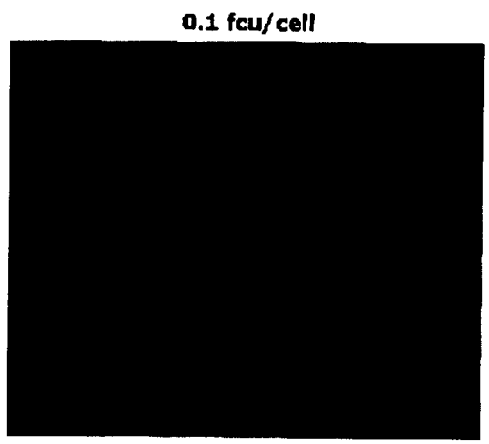
FIG. 18 shows E1-dependent expression of pIX-EGFP in A549 cells. A549 human lung cancer cells were infected with a replication-deficient E1- and E3-deleted control Ad-IX-EGFP and a replication competent Ad-wt-IX-EGFP at 0.1 and 0.01 fcu/cell. Three days post-infection, the cells were imaged for expression of pIX-EGFP.
Figure 18:
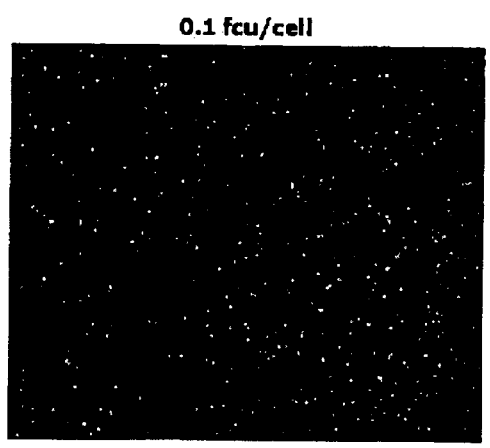
Figure 18:
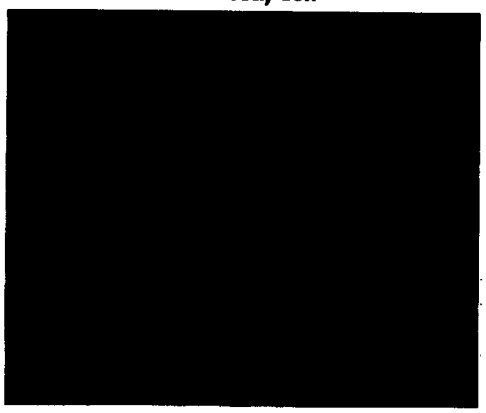
Figure 18:

To more stringently show the utility of pIX-EGFP as an accurate indicator of viral replication, a wild-type adenovirus with the IX-EGFP gene (Ad-wt-IX-EGFP) was constructed and tested in A549 human lung cancer cell line. The E1- and E3-deleted replication-incompetent Ad-IX-EGFP virus which was characterized as described above was chosen as a negative control for replication. Three days post-infection at 0.1 and 0.01 fcu/cell, no pIX-EGFP expression in A549 cells was detected for the replication-deficient virus. However, in experiments described above, expression was observed for this virus in 911 cells expressing E1 genes for complementation. Unlike the replication-deficient virus, pIX-EGFP expression was notable in A549 for the wild-type virus containing the IX-EGFP gene (FIG. 18). These results indicate that expression of pIX-EGFP relies on the presence of the E1 proteins, specifically the 21 kDa E1B protein, the E1a 12S and 13S proteins as well as E4 products. The implications of this finding is highly relevant for conditionally replicative adenoviruses (CRAds) considering the fact that most of the advanced generation CRAds have been designed with tumor specific promoters driving the expression of E1a gene as the checkpoint of replication. pIX-EGFP would serve as an accurate signal of replication for these E1a-controlled replicative agents.

EXAMPLE 13
Construction of Core-Labeled Adenovirus

Since adenovirus with modifications of the core proteins have not been previously described, the inventors first constructed chimeric recombinant adenoviruses expressing both the EGFP fusion core proteins and the wild-type proteins. This conservative strategy ensures the rescue of viruses should the fusion protein by itself cannot functionally substitute for the native one. Initially, the inventors made constructs with a constitutive CMV promoter driving the expression of mat-mu-EGFP (mature form), V-EGFP, pre-VII-EGFP (premature form), and mat-VII-EGFP (mature form) from a deleted E1 region. All of these cassettes were obtained from David Matthews (University of Bristol, Bristol, UK) in a pcDNA3 plasmid. Because the configurations from the parent plasmids are similar, mu-EGFP, V-EGFP, pre-VII-EGFP, and mat-VII-EGFP were cut out with ApaI/blunted and KpnI and ligated into pShuttle-CMV linearized with KpnI and EcoRV. Correct clones were identified by restriction analysis along with verification of fusion protein expression. All shuttle plasmids were linearized with PmeI prior to homologous recombination with pAdEasy-1 to produce the final recombinant adenoviral backbones.

It is known that efficient expression of adenoviral proteins during infection is dependent on the splicing event of a "tripartite leader sequence" (TLS) onto the 5' ends of viral mRNA transcripts, giving translation preference to viral transcripts over cellular ones. The addition of this sequence to expression cassettes has been shown to enhance expression during virus replication. Because expression of the core fusion proteins from E1 by a CMV promoter would lack this tripartite leader sequence, the level of the fusion protein expression would be much lower than that of the wild-type protein expressed from its natural major late promoter. Too low expression of the fusion protein label would put it at a disadvantage for packaging if it has to compete with very high levels of natural protein. To circumvent this problem, a pAdenoVator-CMV5 (Qbiogene, Carlsbad, Calif.) shuttle vectors expressing the fusion core proteins by a CMV promoter with the adenoviral TLS upstream of the transgene was constructed. The cloning involved moving BglII-BstXI fragments from the above E1 pShuttle vectors containing the fusion core proteins into pAdenoVator-CMV5 linearized with BamHI and BstXI. pAdenoVator-CMV5-V-EGFP, however, was made by cloning a SalI/blunted and BstXI fragment from pShuttle-CMV-V-EGFP into pAdenoVator-CMV5 cut with PmeI and BstXI. All pAdenoVator-CMV5 shuttle plasmids were linearized with BbsI and EcoRI before homologous recombination with pAdEasy-1.

Another issue to consider when using the CMV promoter to express the fusion core proteins is the fact that untimely early expression of the structural proteins mu, V, and VII, all of which bind to viral DNA, may hamper both DNA replication and transcription. To avoid this problem, viruses can be constructed to express the fusion core proteins from the E3 region (without a CMV promoter), expression from which has been shown to mimic the expression profile of the major late promoter (MLP). Furthermore, transcripts from this region would automatically be spliced with the TLS to give high and efficient expression of the transgene. All fusion core proteins (except V-EGFP) were cloned from their pShuttle plasmids as BglII-HpaI fragments into pShuttlE3 cut with SalI/blunted and BamHI. Fusion core protein V-EGFP was transferred from pcDNA3-CMV-V-EGFP as an NruI-SphI fragment (without CMV) and put into pABS.4 cut with EcoRI/blunted and SphI. From there, the V-EGFP gene was moved into pShuttlE3 using XhoI-SphI partial cutting. pShuttlE3 contains left and right homologous arms from pBHG10 (Microbix, Toronto, CAN) flanking a deleted E3 region substituted with a kanamycin gene and multiple cloning site. Recombination of the MscI linearized pShuttlE3 vectors was done with pTG3602 (backbone containing the entire wild-type Ad5 sequences, Transgene, Cedex, France) using Amp/Kan selection to yield backbones with wild-type E1 and an E3 region replaced with the fusion core genes. SwaI or ClaI was used to cut out the Kan gene before using the backbone for virus generation.

Figure 19:
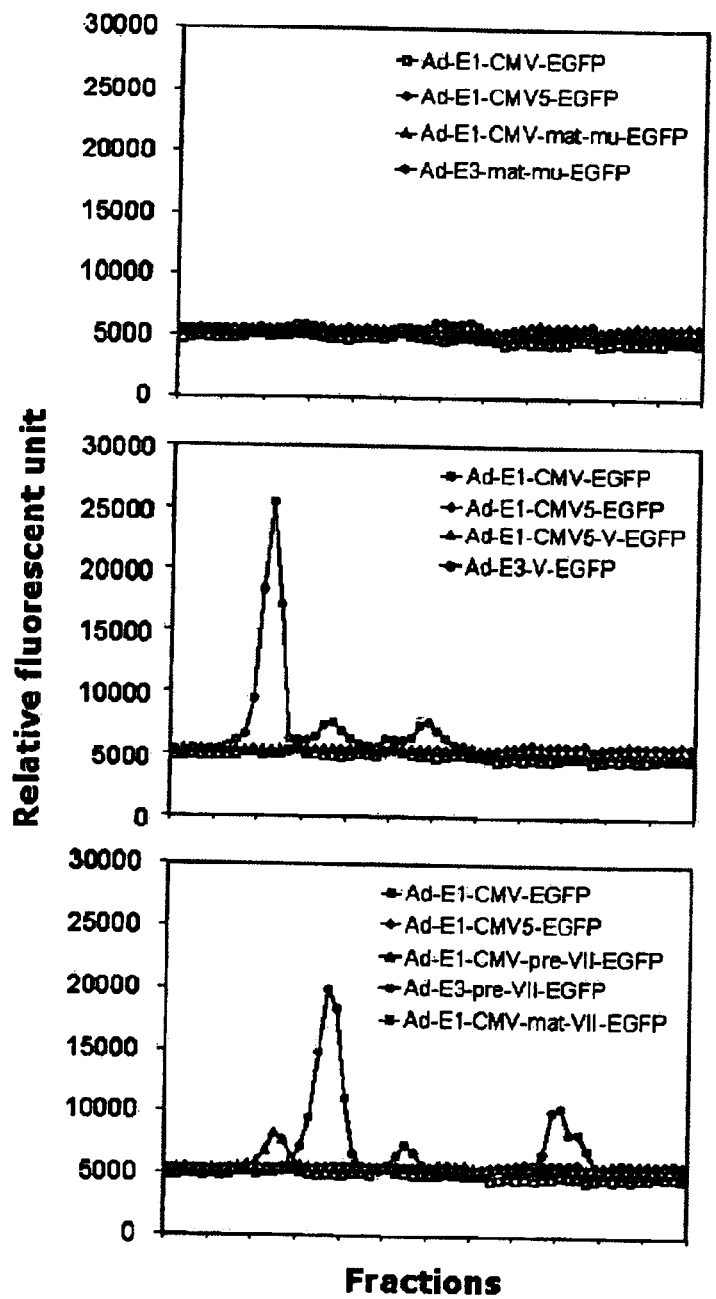
FIG. 19 shows the fluorescent of core protein-labeled adenoviruses. Adenoviruses were constructed with E1-CMV, E1-CMV5 (tripartite leader sequence included), and E3 expression cassettes for mat-mu-EGFP, V-EGFP, pre-VII-EGFP, and mat-VII-EGFP (pre=premature, mat=mature). All but Ad-E1-CMV5-mat-mu-EGFP, Ad-E1-CMV5-pre-VII-EGFP, Ad-E1-CMV5-mat-VII-EGFP, and Ad-E3-mat-VII-EGFP were rescued. Fluorescence of gradient fractions of each virus were measured. 5000 RFU represents the background fluorescence.

All viruses were propagated initially in 911 cells and finally in ten 15 cm dishes of 293 cells. Crude viral lysates were ultracentrifuged and gradient fractions were collected for fluorescence analysis as described above. As shown in FIG. 19, positive labeling was observed for viruses expressing V-EGFP and pre-VII-EGFP from E3.

EXAMPLE 14
Dynamic Monitoring of Virus Replication and Spread in an Organotypic Culture System A raft culture system has been validated as an organotypic in vitro culture system for adenovirus replication (Balague et al., 2001). This organotypic raft culture system can be used to observe the replication and spread of labeled adenoviruses in a three-dimensional environment more representative of in vivo conditions. Normal neonatal foreskin keratinocytes can be isolated from primary samples and infected with fluorescent-labeled viruses at low moi's (0.01 and 0.001 fcu/cell). These infected cells are then transferred onto dermal equivalents consisting of type 1 rat tail collagen (Collaborative Research) and Swiss 3T3 J2 fibroblasts. Viral replication and spread can be monitored over 10 days as the culture is allowed to grow at the air-medium interface. Images can be acquired with an epifluorescence microscope as described previously. Fields of interest can be conserved over the course of imaging to provide a dynamic representation of the replication and lateralization process in chosen areas.

Alternatively, laser confocal scanning microscopy which can achieve thin optical section imaging of samples as thick as 100 um can be used for imaging. Resulting confocal images would be sharp with greater contrast unlike images captured with conventional microscopy that are degraded and blurred by out of focus signals. An extension of confocal microscopy is the use of a multiphoton light source in exciting a fluorophore to obtain more specific signal detection in specimens up to 400 um (Nitschke and Ricken, 1999). Either of these alternatives will aid the imaging of replication and spread in a thick multi-layered organotypic culture.

EXAMPLE 15
Noninvasive Detection of Replication and Spread In Vivo Using Xenograft Tumor Model The ability to view real-time molecular events in their physiological milieu represents the ultimate tool to study biology and medicine. Despite the fact that in vitro studies can serve as a simplified controlled model to study the behavior of replicative adenoviruses in tumor cells, their simplicity strips them of the complexities of a three-dimensional tumor environment that has profound effects on the performance of the viral agents. Ultimately, highest yield of valuable information about oncolytic adenoviruses will have to come from the study and application in patients. Obtaining this information necessitates the capacity to determine whether or not the agent is replicating, replicating specifically, and spreading. If at all possible, such monitoring should be accomplished without the need for invasive procedures such as biopsies which are error-prone and cannot give a full representation of the whole tumor. Furthermore, the ability to noninvasively observe oncolytic adenoviral function on a whole-body level allows the possibility of detecting virus dissemination outside of the tumor.

Recent advances in the field of molecular imaging has afforded the possibility to examine biological phenomena in live animals with potential for translational use in patients (Weissleder and Ntziachristos, 2003; Weissleder and Mahmood, 2001). With regards to fluorescence optical imaging, several groups have utilized GFP to detect tumor growth and metastases as well as gene expression on a whole-body level (Yang et al., 2000a, 2000b; Hoffman, 2001). Data presented above have identified one or several structural labeling strategies which yield detectable fluorescently labeled viral particles, preserve viral replication, lysis, and lateralization functions, and accurately represent the level of replication or progeny production. Wild-type adenoviruses incorporating labeling motif(s) disclosed herein can be constructed and tested in a subcutaneous tumor xenograft mouse model for noninvasive monitoring.

Subcutaneous Tumor Xenograft Mouse Model

Subcutaneous (s.c.) tumors can be established in athymic nude mice by inoculating $3 \times 10^6$ A549 human lung cancer cells. Once the s.c. tumors reach 5–7 mm, $10^9$ viral particles of wild-type labeled adenoviruses can be injected directly into the tumor. E1- and E3-deleted viruses with corresponding structural fusion genes can be used as replication-defective controls.

Noninvasive Monitoring of Viral Replication and Spread

Noninvasive imaging of replication and spread can be performed as previously described (Chaudhuri et al., 2001a, b). Briefly, both bright field and fluorescent images of the tumor can be acquired daily over the course of 10 days using a Leica stereomicroscope (Leica MZ FLIII, Vashaw Scientific, Inc., Atlanta, Ga.) equipped with a Cool Snap-Pro color digital camera (Media Cybernetics, Del Mar, Calif.). The noninvasive images are captured with the mouse in the same position from day to day to demonstrate the dynamics of replication and spread. Images are processed and analyzed with Image Pro Plus 4.5 software (MediaCybernetics, Carlsbad, Calif.) to assess augmentation of intensity and size of the fluorescent signal.

Histological Validation of Viral Replication and Spread

Tumors are dissected at the end of ten days and processed by tissue frozen section (5 μm), fixed with 3% formaldehyde, nuclear stained with Hoechst dye, and mounted on coverslip slides for fluorescence microscopy of the fluorescent fusion protein signal. Tissue-sectioned images can be compared to the corresponding noninvasive ones for correlation. Likewise, a number of reserve animals can be sacrificed earlier than 10 days to show earlier illustrations of replication and spread.

Evaluation of Imaging in Orthotopic Tumor Model

Cross-species replication restrictions requires that adenoviral agents be studied in human tumor/SCID systems. Thus, imaging of labeled adenoviruses can be tested in an orthotopic model of ovarian cancer. The ovarian cancer cell line SKOV3ip.1 can be injected orthotopically into SCID mice via intraperitoneal injection. Ten days post-implantation the animals would manifest a clinical context comparable to human ovarian cancer. At this juncture the animals can be challenged with labeled adenoviral agents. Various doses of the viral agents can be administered, and the animals are studied at various point post-viral administration. Replication defective Ads encoding EGPF are employed as control. Analysis will include study of tumor nodules and normal adenoviral organs for fluorescent activity via fluometric methods as well as direct fluorescent microscopy. Results from these studies would provide a database of key functional parameters for this imaging modality and allow a full understanding of the capacity of this imaging modality in the context of a stringent tumor model.

The following references were cited herein:

Balague et al., Human papillomavirus E6E7-mediated adenovirus cell killing: selectivity of mutant adenovirus replication in organotypic cultures of human keratinocytes. J Virol. 75:7602–11 (2001).

Bevis and Glick, Rapidly maturing variants of the *Discosoma* red fluorescent protein (DsRed). Nat Biotechnol. 20:83–7 (2002).

Bhaumik and Gambhir, Optical imaging of *Renilla* luciferase reporter gene expression in living mice. Proc Natl Acad Sci USA. 99:377–82 (2002).

Burbelo et al., Detecting protein-protein interactions using *Renilla* luciferase fusion proteins. Biotechniques 33:1044–8, 1050 (2002).

Campbell et al., A monomeric red fluorescent protein. Proc Natl Acad Sci USA. 99:7877–82 (2002).

Chartier et al., Efficient generation of recombinant adenovirus vectors by homologous recombination in *Escherichia coli*. J. Virol. 70:4805–4810 (1996).

Chaudhuri et al., A noninvasive reporter system to image adenoviral-mediated gene transfer to ovarian cancer xenografts. Gynecol Oncol. 83:432–8 (2001a).

Chaudhuri et al., Light-based imaging of green fluorescent protein-positive ovarian cancer xenografts during therapy. Gynecol Oncol. 82:581–9 (2001b).

Diehn et al., Noninvasive fluorescent imaging reliably estimates biomass in vivo. Biotechniques 33:1250–2, 1254–5 (2002).

Dmitriev et al., Engineering of adenovirus vectors containing heterologous peptide sequences in the C terminus of capsid protein IX. J Virol. 76:6893–9 (2002).

Gross et al., The structure of the chromophore within DsRed, a red fluorescent protein from coral. Proc Natl Acad Sci USA. 97:11990–5 (2000).

Gurskaya et al., GFP-like chromoproteins as a source of far-red fluorescent proteins. FEBS Lett. 507:16–20 (2001).

He et al., A simplified system for generating recombinant adenoviruses. Proc Natl Acad Sci USA. 95:2509–14 (1998).

Hoffman, Visualization of GFP-expressing tumors and metastasis in vivo. Biotechniques 30:1016–22, 1024–6 (2001).

Ilyin et al., Fiber-optic monitoring coupled with confocal microscopy for imaging gene expression in vitro and in vivo. J Neurosci Methods 108:91–6 (2001).

Nitschke and Ricken, 2-Photon Microscopy—the Future of Fluorescence Microscopy? Innovation (1999).

Rooney et al., Laser fluorescence bronchoscopy for detection of fluorescent reporter genes in airway epithelia. Gene Ther. 9:1639–44 (2002).

Wang et al., Renilla luciferase-Aequorea GFP (Ruc-GFP) fusion protein, a novel dual reporter for real-time imaging of gene expression in cell cultures and in live animals. Mol Genet Genomics 268:160–8 (2002).

Weissleder and Ntziachristos, Shedding light onto live molecular targets. Nat Med. 9:123–8 (2003).

Weissleder and Mahmood, Molecular imaging. Radiology 219:316–33 (2001).

Yamamoto et al., Infectivity Enhanced, Cyclooxygenase-2 Promoter-Based Conditionally Replicative Adenovirus for Pancreatic Cancer. In submission.

Yang et al., Whole-body optical imaging of green fluorescent protein-expressing tumors and metastases. Proc Natl Acad Sci USA. 97:1206–11 (2000a).

Yang et al., Visualizing gene expression by whole-body fluorescence imaging. Proc Natl Acad Sci USA 97:12278–82 (2000b).

Yang et al., Direct external imaging of nascent cancer, tumor progression, angiogenesis, and metastasis on internal organs in the fluorescent orthotopic model. Proc Natl Acad Sci USA. 99:3824–9 (2002).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of increasing the ability of an adenovirus to transduce a specific cell type relative to an unmodified adenovirus, comprising the step of: modifying a gene encoding an adenoviral capsid protein by introducing a DNA sequence encoding a single chain antibody into the 3' end of the minor capsid protein pIX gene, wherein said modification increases the ability of said adenovirus to transduce a specific cell type relative to an unmodified adenovirus.

2. The method of claim 1, wherein said single chain antibody is directed towards a protein, wherein said protein is specific to a cell type.

3. The method of claim 2, wherein said cell type is a tumor cell.

4. The method of claim 2, wherein said protein is a cell-surface protein.

5. The method of claim 1, wherein said modified capsid protein retains its native display profile.

6. The method of claim 1, wherein said adenovirus exhibits coxsackie adenovirus receptor CAR-independent gene transfer.

7. The method of claim 1, wherein the adenoviral vector encoding said adenovirus further comprises a therapeutic gene.

8. A method of killing tumor cells in an individual, said method comprising the steps of: injecting directly to said tumor cells an effective amount of recombinant adenoviruses comprising a therapeutic gene encoding a protein that converts a non-toxic compound to a toxic compound and a gene encoding a pIIIa protein or a pIX protein modified by introducing a single chain antibody into the N-terminus of said pIIIa protein or the C-terminus of said pIX protein; and treating said individual with said non-toxic compound.

9. The method of claim 8, wherein said therapeutic gene is herpes simplex virus-thymidine kinase gene and said non-toxic compound is ganciclovir.

10. The method of claim 8, wherein said single chain antibody is directed towards a protein specific to a cell type.

11. The method of claim 10, wherein said cell type is a tumor cell.

12. The method of claim 10, wherein said protein is a cell-surface protein.

13. The method of claim 8, wherein said modified capsid protein retains its native display profile.

* * * * *

SEQUENCE LISTING

```
<160> NUMBER OF SEQ ID NOS: 9

<210> SEQ ID NO 1
<211> LENGTH: 8
<212> TYPE: PRT
<213> ORGANISM: Unknown
<220> FEATURE:
<221> NAME/KEY: CHAIN
<222> LOCATION:
<223> OTHER INFORMATION: Flag peptide tag

<400> SEQUENCE: 1

Asp Tyr Lys Asp Asp Asp Asp Lys
                5               8

<210> SEQ ID NO 2
<211> LENGTH: 25
<212> TYPE: DNA
<213> ORGANISM: Artificial Sequence
<220> FEATURE:
<221> NAME/KEY: primer_bind
<223> OTHER INFORMATION: primer pIIIaN.F for introducing six histidine
      tag into the pIIIa protein

<400> SEQUENCE: 2
cgcgaggagg tggctatagg actga                                           25

<210> SEQ ID NO 3
<211> LENGTH: 36
<212> TYPE: DNA
<213> ORGANISM: Artificial Sequence
<220> FEATURE:
<221> NAME/KEY: primer_bind
<223> OTHER INFORMATION: primer pIIIaN6His.L for introducing six
      histidine tag into the pIIIa protein

<400> SEQUENCE: 3
atggtgatgg tgatggtgca tctgatcaga aacatc                               36

<210> SEQ ID NO 4
```

```
<211> LENGTH: 22
<212> TYPE: DNA
<213> ORGANISM: Artificial Sequence
<220> FEATURE:
<221> NAME/KEY: primer_bind
<223> OTHER INFORMATION: primer pIIIaN.R for introducing six histidine
      tag into the pIIIa protein

<400> SEQUENCE: 4
ttcggccagc gcgtttacga tc                                            22

<210> SEQ ID NO 5
<211> LENGTH: 32
<212> TYPE: DNA
<213> ORGANISM: Artificial Sequence
<220> FEATURE:
<221> NAME/KEY: primer_bind
<223> OTHER INFORMATION: primer pIIIaN6His.U for introducing six
      histidine tag into the pIIIa protein

<400> SEQUENCE: 5
caccatcacc atcaccatat gcaagacgca ac                                 32

<210> SEQ ID NO 6
<211> LENGTH: 24
<212> TYPE: DNA
<213> ORGANISM: Artificial Sequence
<220> FEATURE:
<221> NAME/KEY: primer_bind
<223> OTHER INFORMATION: Sense PCR primer N6His.U complementary to
      6His coding sequence

<400> SEQUENCE: 6
atgcaccatc accatcacca tatg                                          24

<210> SEQ ID NO 7
<211> LENGTH: 30
<212> TYPE: DNA
<213> ORGANISM: Artificial Sequence
<220> FEATURE:
<221> NAME/KEY:
<223> OTHER INFORMATION: Oligonucleotide FLAGc.U designed to form DNA
      duplex coding for Flag peptide

<400> SEQUENCE: 7
ctgccgatta taaggatgac gatgacaagt                                    30

<210> SEQ ID NO 8
<211> LENGTH: 30
<212> TYPE: DNA
<213> ORGANISM: Artificial Sequence
<220> FEATURE:
<221> NAME/KEY:
<223> OTHER INFORMATION: Oligonucleotide FLAGc.L designed to form DNA
      duplex coding for Flag peptide

<400> SEQUENCE: 8
acttgtcatc gtcatcctta taatcggcag                                    30

<210> SEQ ID NO 9
<211> LENGTH: 22
<212> TYPE: DNA
<213> ORGANISM: Artificial Sequence
<220> FEATURE:
<221> NAME/KEY: primer_bind
<223> OTHER INFORMATION: PCR primer
```

```
<400> SEQUENCE: 9
agttgacggc tcttttggca ca                                                    22
```